United States Patent [19]

Chirikjian et al.

[11] Patent Number: 5,763,178
[45] Date of Patent: *Jun. 9, 1998

[54] OSCILLATING SIGNAL AMPLIFIER FOR NUCLEIC ACID DETECTION

[75] Inventors: Jack G. Chirikjian, Potomac; G. Bruce Collier, Gaithersburg, both of Md.

[73] Assignee: Trevigen, Inc., Gaithersburg, Md.

[*] Notice: The term of this patent shall not extend beyond the expiration date of Pat. No. 5,656,430.

[21] Appl. No.: 663,023

[22] Filed: Jun. 7, 1996

Related U.S. Application Data

[63] Continuation-in-part of Ser. No. 483,089, Jun. 7, 1995, Pat. No. 5,656,430.
[51] Int. Cl.$^6$ .............................. C12Q 1/68; C07H 21/02; C07H 21/04; C12N 15/00
[52] U.S. Cl. .............................. 435/6; 536/23.1; 536/24.3; 935/72; 935/78
[58] Field of Search .............................. 435/6; 536/23.1, 536/24.3; 935/77, 78

[56] References Cited

U.S. PATENT DOCUMENTS

| | | | |
|---|---|---|---|
| 4,876,187 | 10/1989 | Duck et al. | 1/68 |
| 5,011,769 | 4/1991 | Duck et al. | 1/68 |
| 5,459,039 | 10/1995 | Modrich et al. | 435/6 |
| 5,556,750 | 9/1996 | Modrich et al. | 435/6 |
| 5,656,430 | 8/1997 | Chirikjian et al. | 435/6 |

FOREIGN PATENT DOCUMENTS

| | | | |
|---|---|---|---|
| WO 93-02216 | 4/1993 | WIPO | 1/68 |
| WO 93 20233 | 10/1993 | WIPO | |
| WO 95/07361 | 3/1995 | WIPO | |
| WO 95/12688 | 5/1995 | WIPO | |
| WO 95/14106 | 5/1995 | WIPO | |

OTHER PUBLICATIONS

Duck et al. "Probe Amplifier System Based on Chimeric Cycling Olignoucleotides", *Bio Techniques*, 9(2):142–147 (1990).

Hsu et al. "Detection of DNA Point Mutations with DNA Mistmatch Repair Enzymes", *Carcinogensis*, 15(8):1657–1662 (1994).

Lu et al. "Detection of Single DNA Base Mutations with Mismatch Repairs Enzymes", *Genomics*14, pp. 249–255 (1992).

Wu et al. "*Escherichia Coli*MutY protein has both N–glycosylase and apurinic. . . ", *Pro, Natl. Acad. Sci.*, 89:8779–8783 (1992).

Bruice et al. "A Comparison of the Bimolecular and Intramolecular Nucleophilic Catalysis . . . ", *Journal of American Chemical Society*, vol. 85:1 (1963).

Corey et al. "Generation of a Hybrid Sequence–Specific Single–Stranded Deoxyribonuclease", *Science*, 238:1401 (1987).

Corey et al. "Sequence–Selective Hydrolysis of Duplex DNA By An Oligonucleotide–Directed Nuclease", *American Chemical Society*, vol. 111, 8523 (1989).

Deng et al. J.A. Anal. Biochem. 200:81 (1992).

Hanvey et al. "Antisense and Antigene Properties of Peptide Nucleic Acids", *Science*, vol. 258, pp. 1482–1485 (1992).

Kunkel "The Efficiency of Oligonucleotide–Directed Mutagenesis", *Nucleic Acids Mol. Biol.*, 12:124 (1988).

Kunkel "Rapid And Efficient Site–Specific Mutagenesis Without Phenotypic Selection", *Proc. Natl. Acad. Sci. USA*, vol. 82, pp. 488–492 (1985).

Nölling et al. "Modular Organization of Related Archaeal Plasmids Encoding Different Restriction –Modification . . . ." *Nucleic Acids Research*, vol. 20, No. 24, pp. 6501–6507 (1992).

Wittung et al. "DNA–like Double Helix Formed By Peptide Nucleic Acid", *Nature*, vol. 368, pp. 561–563 (1994).

Zinder et al. "The Filiamentous Phage (Ff) As Vectors for Recombinant DNA–A Review", *Gene*, 19 (1982).

Lu et al. "Detection of Single DNA Base Mutations with Mismatch Repair Enzymes, " *Genomics*, 14, No. 2 pp. 249–255 (1992).

Hsu et al. "Detection of DNA Point Mutations with DNA Mismatch Repair Enzymes, " *Carcinogenesis*, vol. 15, No. 8, pp. 1657–1662 (1994).

Yao et al. "Strand–Specific Cleavage of Mismatch–Containing DNA By Deoxyinosine 3' –Endonuclease from *Escherichia coli*, " Journal of Biological Chemistry, vol. 269, No. 50, pp. 31390–31396 (1994).

Au et al. "*Escherichia Coli Mut*YGene Product is Required for Specific A–G → C.G Mismatch Correction, " *Proc. Natl. Acad. Sci. USA*, vol. 85, pp. 9163–9166 (1988).

(List continued on next page.)

*Primary Examiner*—W. Gary Jones
*Assistant Examiner*—Ethan Whisenant
*Attorney, Agent, or Firm*—Foley & Lardner

[57] ABSTRACT

The present invention provides several methods employing nucleic acid repair enzymes. The present invention provides a method for detecting point mutations in nucleic acid sequences. The present invention further provides a method for detecting non-mutated or wild-type nucleic acid sequences. The present invention also enhances target polynucleotide detection using an oscillation reaction and tail labeling techniques, as well as by linking the nucleic acid repair enzyme to a probe molecule. The present invention also provides helix destabilizing molecule and similar molecules to enhance the hybridization of the probe to the target polynucleotides. This invention further provides for the use of thermally stable nucleic acid repair enzymes which will facilitate reactions at elevated temperatures. This invention also provides a method for determining the repair index for a mismatched or damaged oligonucleotide probe. Finally, this invention renders a method for effecting in vitro mutagenesis of a target polynucleotide.

24 Claims, 12 Drawing Sheets

OTHER PUBLICATIONS

Tsai–Wu et al. "*Escherichia Coli*MutY Protein has Both N–Glycosylase and Apurinic/Apyrimidinic Endonuclease Activities on A.C and A.G Mispairs ," *Proc. Natl. Acad. USA*, vol. 89, pp. 8779–8783 (1992).

Youil et al. "Screening for Mutations By Enzymes Mismatch Cleavage with T4 Endonuclease VII", *Pro. Natl. Acad. Sci., USA*, vol. 92, pp. 87–91 (1995).

Corey et al. "Sequence–Selective Hydrolysis of Duplex DNA By an Oligonucleotide–Directed Nuclease, " *J. Am. Chem. Soc.* 1989, vol. 111, pp. 8523–8525 (1989).

Nölling et al. Modular Organization of Related Archaeal Plasmids Encoding Different Restriction–Modification Systems in *Methanobacterium Thermoformicicum*, Nucleic Acids Research, vol. 20, No. 24, pp. 6501–6507 (1992).

Lahue et al., Science 245 : 160–164 (1989).

FIG. 11A

```
ATG GAT GAT GCT ACT AAT AAA AAA AGG AAA GTC TTC GTT AGC ACC ATA      48
Met Asp Asp Ala Thr Asn Lys Lys Arg Lys Val Phe Val Ser Thr Ile
 1                   5                  10                  15

CTT ACG TTT TGG AAT ACA GAT AGG CGC AGG GAC TTT CCT TGG AGG CAT ACG  96
Leu Thr Phe Trp Asn Thr Asp Arg Arg Arg Asp Phe Pro Trp Arg His Thr
             20                  25                  30

AGG GAC CCC TAT GTA ATT TTA ATA ACG GAA ATC CTA CTT CGC AGG ACA     144
Arg Asp Pro Tyr Val Ile Leu Ile Thr Glu Ile Leu Leu Arg Arg Thr
        35                  40                  45

ACT GCG GGG CAT GTT AAA AAG ATA TAT GAC AAG TTT GTT AAG TAC         192
Thr Ala Gly His Val Lys Lys Ile Tyr Asp Lys Phe Val Lys Tyr
    50                  55                  60

AAG TGC TTT GAG GAT ATA TTA AAA ACG CCA AAA TCA GAA ATC GCC AAA     240
Lys Cys Phe Glu Asp Ile Leu Lys Thr Pro Lys Ser Glu Ile Ala Lys
65                  70                  75                  80
```

FIG. 11B

```
GAC ATA AAA GAA ATC GGA CTC TCT AAC CAA AGG GCA GAA CAG CTA AAA    288
Asp Ile Lys Glu Ile Gly Leu Ser Asn Gln Arg Ala Glu Gln Leu Lys
            85                      90                      95

GAA CTG GCA AGG GTC GTC ATA AAT GAT TAT GGG GGC AGA GTG CCC CGA    336
Glu Leu Ala Arg Val Val Ile Asn Asp Tyr Gly Gly Arg Val Pro Arg
        100                     105                     110

AAT AGG AAG GCA ATT TTA GAT CTA CCA GGA GTT GGC AAA TAC ACT TGT    384
Asn Arg Lys Ala Ile Leu Asp Leu Pro Gly Val Gly Lys Tyr Thr Cys
        115                     120                     125

GCT GCA GTT ATG TGT TTG GCA TTT GGC AAA AAA GCC GCT ATG GTC GAT    432
Ala Ala Val Met Cys Leu Ala Phe Gly Lys Lys Ala Ala Met Val Asp
    130                     135                     140
```

FIG. 11C

```
GCA AAT TTT GTG AGA GTT ATT AAC AGG TAC TTT GGG GGA AGC TAT GAA    480
Ala Asn Phe Val Arg Val Ile Asn Arg Tyr Phe Gly Gly Ser Tyr Glu
145                 150                 155                 160

AAC CTG AAC TAC AAC CAC AAG GCC CTG TGG GAA CTT GCG GAG ACC CTT    528
Asn Leu Asn Tyr Asn His Lys Ala Leu Trp Glu Leu Ala Glu Thr Leu
                165                 170                 175

GTA CCT GGC GGA AAG TGC AGG GAC TTT AAC CTT GGT TTA ATG GAC TTT    576
Val Pro Gly Gly Lys Cys Arg Asp Phe Asn Leu Gly Leu Met Asp Phe
            180                 185                 190

TCC GCA ATC ATA TGT GCC CCA AGA AAG CCA AGA TGT GAG AAA TGT GGG    624
Ser Ala Ile Ile Cys Ala Pro Arg Lys Pro Arg Cys Glu Lys Cys Gly
        195                 200                 205

ATG AGC AAA CTC TGT AGC TAC TAT GAG AAG TGT AGT ACT TGA            666
Met Ser Lys Leu Cys Ser Tyr Tyr Glu Lys Cys Ser Thr *
    210                 215                 220
```

OSCILLATING SIGNAL AMPLIFIER FOR NUCLEIC ACID DETECTION

This application claims the benefit of U.S. provisional application Ser. No. 60/012,950, filed Mar. 6, 1996, now abandoned. This application is also a continuation-in-part of application Ser. No. 08/483,089, filed Jun. 7, 1995 now U.S. Pat. No. 5,656,430.

BACKGROUND OF THE INVENTION

Genomic DNA provides the template for the information that allows the generation of proteins which are expressed and made by an organism. These proteins are generally essential for the survival of any specific cell in an organism. Therefore, the organism requires the template to be correct and free of mistakes in order to generate a protein that is functional in a cell. If a single nucleotide of this DNA sequence is mutated (a "point mutation"), the protein may be nonfunctional. Point mutations which elicit disease states are known for many proteins. Examples include sickle cell anemia hypoxanthine phosphotransferase, and p53, a tumor suppressor gene, and several oncogenes and cancer genes.

A review by Cotton, *Biochem. J.* 263: 1 (1989), compared several methodologies for detection of point mutations with respect to the DNA type used, the DNA stage achieved, whether the mutation position was detected, the percentage of mutations detected, the time and cost requirements, and toxicity problems. Each of the methodologies examined by Cotton presents drawbacks. DNA sequencing, for example, is time consuming and expensive. Restriction enzymes do not define the mutation position and detect less than 50% of mutations. Denaturing gradient gels and SSCP, see Murakami et al., *Cancer Res.* 51: 3356 (1981), do not define the mutation position and are not efficient at detecting mutations. S1 nuclease and RNAse are not efficient at detecting mutations. Finally, Carbodi-imide/ABC nuclease and carbodi-imide are efficient but generate false positives and are toxic.

Recently, point mutations have been detected with the *E. coli* repair enzyme mutY. See Hsu et al., *Carcinogenesis* 15(8): 1657 (1994). In this method a wild type labeled probe is generated using the polymerase chain reaction (PCR) described, for example, by Saiki et al., *Nature* 324: 163 (1986). The probe then is hybridized to the unknown sample DNA wherein mutY then cleaves mismatches when an adenosine which does not form watson crick base pairing with a guanine nucleotide. The position of mutY cleavage at A/G sites can then be determined by gel electrophoresis. This methodology is limited by the use of PCR, which itself generates mutations in the amplified DNA. See Loeb et al., *Nucleic Acids & Molec. Biol.* 1: 157 (1987); Tindal et al., *Biochemistry* 27: 6008 (1988); Kunkel, loc. cit. 29: 8004 (1990).

Accordingly, there is a need for an accurate and efficient method of detecting point mutations using unamplified DNA source molecules. In addition, such a method would save time, require minimal equipment and is less expensive, as well decreasing the hazard of toxic chemicals. Also, methods of amplifying limiting amounts of the mutated sequences would have advantages. By the same token, there is a need for accurate and inexpensive methods to detect non-mutated target polynucleotides from unamplified DNA source molecules.

Currently there are several amplification methodologies, well known to those skilled in the art, for the detection of non-mutated DNA. Among these techniques are the polymerase chain reaction (PCR), the ligase chain reaction (LCR), nucleic acid system-based amplification (NASBA), and cycling probe technology (CPT). Other amplification methods are well known to those skilled in the art.

The polymerase chain reaction described, for example, in U.S. Pat. No. 4,362,195, is the best known amplification system, but it is limited by the level of amplification ($\sim 2.2 \times 10^5$), is prone to the generation of mutations, and can generate false positives by the generation of amplified molecules contaminating the environment. Despite these limitations, PCR is widely used in the research community. It still is not approved by governmental regulators for clinical and diagnostic applications, however.

CPT technology was developed, in part to overcome the limitations of PCR. See, for example, U.S. Pat. No. 4,876,187 and U.S. Pat. No. 5,011,769. The CPT technology entails the use of a synthetic molecule with two non-complementary nucleic acid sequences joined by a scissile linkage. CPT technology works by observing a hybridization event with a sample nucleic acid by a single cleavage event. This technology utilizes both the enzymatic features of RNAse H and a synthetic DNA-RNA-DNA oligonucleotide. RNAse H specifically cleaves the RNA moiety of the DNA-RNA-DNA oligonucleotide only when it is perfectly hybridized to a complementary DNA target molecule. A high concentration of the DNA-RNA-DNA molecule is converted to cleaved fragments, which are assayed by gel electrophoresis. The level of cleavage indicates the amount of target molecules present in the sample.

The CPT system does not amplify the target, alleviating the accumulation of molecules that in turn become amplifiable and generate false-positives, as occurs in PCR. The CPT technology is linear, in that increasing amounts of target DNA generate linearly more cleaved DNA-RNA-DNA oligonucleotide. (PCR generates exponentially more signal in response to the presence of more target DNA, making quantitation more problematic.) Additionally, CPT can amplify up to $10^6$ cleaved DNA-RNA-DNA probe molecules in about 30 minutes. CPT does not generate more of the target molecule. Therefore, it does not jeopardize the laboratory environment by the possible accumulation of synthesized target DNA molecules, which in turn generate false positive results. It also is isothermal, i.e., it does not require the use of expensive automated thermocycling equipment. Further, it has been shown to detect a single molecule. The CPT technology is limited, however, because the cleavable portion of the molecule is an RNA moiety.

SUMMARY OF THE INVENTION

It is therefore an object of the present invention to provide a method for detecting point mutations in nucleic acid sequences.

It is a further aspect of this invention to provide a simple and efficient, and sensitive method to detect point mutations in nucleic acid sequences.

It is also an object of the invention to provide a means for detecting non-mutated nucleic acid sequences.

It is yet another object of this invention to enhance target polynucleotide detection using oscillating and tagging techniques.

It is an additional object of this invention to provide for thermally stable nucleic acid repair enzymes which will facilitate reactions at elevated temperatures.

Still another aspect of this invention concerns helix destabilizing molecule and similar molecules to enhance the hybridization of the probe to the target polynucleotides.

It is also an object of this invention to provide for the determination of the amount of base repair enzyme activity carried out on a mutated polynucleotide sequence.

Another aspect of this invention relates to the attachment of a nucleic acid repair enzyme to a probe in order to enhance the detection of target polynucleotide and point mutations therein.

It is a further object of this invention to provide for increased specificity in the detection of target nucleotides and point mutations therein, using peptide nucleic acids to construct probes.

In accomplishing the foregoing objects, there is provided a method of detecting a point mutation in a target polynucleotide, comprising:

(a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;

(b) producing probe fragments by cleaving said probe strand of said hybrid polynucleotide at said point of mismatch, wherein said cleaving is effected by a glycosylase attached to said probe and an AP cleaving enzyme; and (c) detecting said probe fragments.

A method of detecting a point mutation in a target polynucleotide, comprising:

(a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;

(b) hybridizing a second and third single-stranded oligonucleotide probe to said target polynucleotide at a location adjacent to said first probe, wherein a glycosylase is attached to said second single-stranded probe and an AP cleaving enzyme is attached to said third single-stranded probe;

(c) producing probe fragments by cleaving said probe strand of said hybrid polynucleotide at said point of mismatch, wherein said cleaving is effected by said glycosylase and AP cleaving enzymes; and (d) detecting said probe fragments.

A method of detecting a sequence in a target polynucleotide, comprising the steps of:

(a) hybridizing a single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence;

(b) producing probe fragments by cleaving said probe strand of said hybrid polynucleotide at said point of mismatch, wherein said cleaving is effected by a glycosylase attached to said probe and an AP cleaving enzyme; and (c) detecting probe fragments produced by said cleavage.

A method of detecting a point mutation in a target polynucleotide, comprising:

(a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;

(b) producing probe fragments by cleaving said probe strand of said hybrid polynucleotide at said point of mismatch, wherein said cleaving is effected by a glycosylase enzyme employed in combination with basic conditions and increased temperature; and (c) detecting said probe fragments.

A method for effecting in vitro mutagenesis of a target polynucleotide, comprising transforming a circular double-stranded nucleic acid molecule, wherein said circular double-stranded nucleic acid molecule is prepared by the steps of:

(a) hybridizing a single-stranded oligonucleotide probe to said target polynucleotide to form a hybrid partially double-stranded circular polynucleotide, wherein said probe is shorter than said target polynucleotide and contains a single base-pair mismatch at a predetermined site;

(b) contacting said hybrid polynucleotide with at least one DNA polymerase and one DNA ligase, whereby a completely double stranded hybrid polynucleotide is formed; and (c) contacting said completely double-stranded hybrid with a nucleic acid repair enzyme, whereby said target polynucleotide strand is cleaved at the site of said point of mismatch.

A method for effecting in vitro mutagenesis of a single-stranded target polynucleotide, comprising:

(a) hybridizing a single-stranded peptide nucleic acid probe to said target polynucleotide to form a hybrid partially double-stranded polynucleotide, wherein said probe is shorter than said target polynucleotide and contains a single base-pair mismatch at a predetermined site;

(b) cleaving said target polynucleotide with a nucleic acid repair enzyme, whereby a gap is introduced into said target polynucleotide;

(c) filling in said gap by contacting said hybrid polynucleotide with at least one DNA polymerase and one DNA ligase; and (d) dissociating said polynucleotide from said PNA probe.

A method of detecting a point mutation in a target polynucleotide, comprising:

(a) hybridizing at least two single-stranded oligonucleotide probes, under stringent conditions, to at least two target polynucleotides to form at least two hybrid double-stranded polynucleotides such that a mismatch occurs at the site of said point mutation, wherein said probes are complementary to a non-mutated sequence of said target polynucleotides, and attached to each probe is a different glycosylase, only one of which will effect cleavage;

(b) producing probe fragments by cleaving one of said probe strands at said point of mismatch, wherein said cleavage is effected by one of said glycosylases and an AP cleaving enzyme; and (c) detecting said probe fragments.

BRIEF DESCRIPTION OF THE FIGURES

In FIG. 6A the enzymes are attached to the 5' ends of the probes, while in FIG. 6B, the enzymes are attached to the 3' ends.

FIG. 11 is a representation of the DNA sequence of orf10 and the amino acid sequence of the corresponding ORF10 polypeptide. (SEQ ID NOS: 16 and 17, respectively).

DETAILED DESCRIPTION OF PREFERRED EMBODIMENTS

Figure 1:
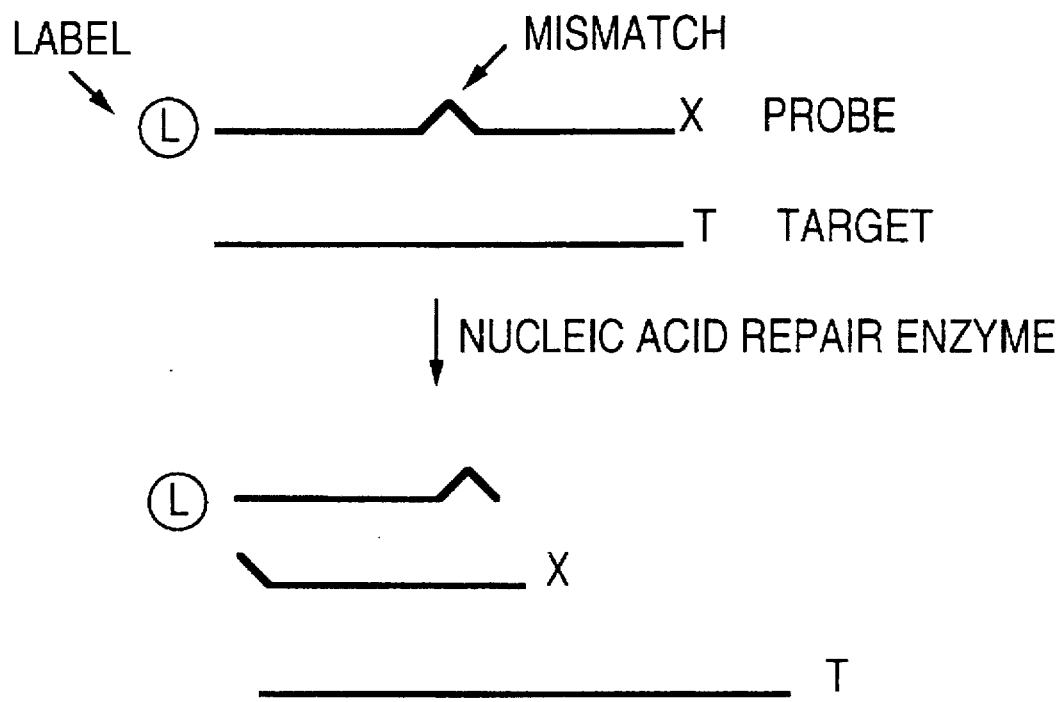
FIG. 1 is a schematic diagram showing the hybridization of probe to target polynucleotide to form a mismatch. The mismatch can be the consequence of either a wild-type probe hybridizing to a mutant target or a mutant probe hybridizing to a wild-type target. Nucleic acid repair enzyme then cleaves the probe, which dissociates from the target.

It has been discovered that the deficiencies in conventional techniques in this regard can be overcome by employing nucleic acid repair enzymes. Thus, the problems by Cotton (1989), *supra*, are avoided by using nucleic acid repair enzymes, in accordance with the present invention, to detect point mutations. Furthermore, nucleotide excision enzymes can be used in the present invention to detect wild-type target polynucleotide sequences and to determine the amount of base repair enzyme activity carried out on a mutated polynucleotide sequence. The present invention represents an improvement over the CPT method, because a DNA oligonucleotide suitable for the present invention can be made via more conventional chemistry (and, hence, is less expensive to synthesize) and is more stable.

Researchers have used nucleic acid repair enzymes to detect point mutations, see Hsu et al. (1994), *supra*, but these techniques are limited because they employ PCR to amplify the target polynucleotide. The present invention overcomes this limitation because it does not require PCR amplification. Instead, nucleic acid repair enzymes can be used to create an oscillating reaction which allows for adequate target detection using a limited amount of unamplified target. Alternatively, detection can be enhanced by using nucleic acid repair enzymes, and other enzymes, to tag the oligonucleotide probe which has bound to the target polynucleotide. Moreover, hybridization of probe to polynucleotide target can be enhanced by employing helix destabilizing molecules, as described in greater detail below.

According to one embodiment of the present invention, point mutations in a target polynucleotide of biological sample can be detected, identified or localized. This embodiment does not include the use of PCR amplification of target polynucleotide, since PCR amplification introduces spurious point mutations.

This embodiment entails hybridizing a single-stranded oligonucleotide probe to a target polynucleotide to form a hybrid, double-stranded polynucleotide. The hybridization occurs under conditions that are "stringent," which typically implicates conditions that include a 50–100 mM salt solution at a temperature of (3N—20° C.), where N is the number of nucleotides in the oligonucleotide probe.

As for probe design, preferably, the oligonucleotide probe is designed not to have self complementary regions, palindromic regions and the probe must also have probe specificity. The parameters for probe design can be found in Lowe et al., *Nucl. Acids Res.* 18:1757–1761 (1990); Rychlik et al., *loc. cit.* 17:8543–8551 (1989); Rychlik et al., *loc. cit.* 18:6409–6412 (1990), which discusses probe design as applied to PCR reactions.

Because the probe is complementary to a non-mutated sequence in the target polynucleotide, there will be a mismatch between non-mutated probe and mutated target polynucleotide. The mismatch will occur at the site of point mutation. The present invention comprehends the existence of multiple sites of mismatch on the hybrid, double-stranded polynucleotide.

The probe is cleaved at the point of mismatch with a "nucleic acid repair enzyme," which is an enzyme that will cleave, at a point of mismatch, one strand of a duplex formed by oligonucleotide probe and target polynucleotide. Examples of nucleic acid repair enzymes are mutY (Wu et al., *Proc. Nat'l Acad. Sci. USA* 89: 8779–83 (1992)), T/G mismatch-specific nicking enzyme from HeLa nuclear extracts (Wiebauer & Jiricny, *Nature* 339: 234–36 (1989); Wiebauer & Jiricny, *loc. cit.* 87: 5842–45 (1990)), T/G mismatch-specific nicking enzyme from *E. coli* (Hennecke et al., *Nature* 353: 776–78 (1991)), human yeast all-type enzymes (Yeh et al., *J. Biol. Chem.* 2667: 6480–84 (1991); Chiang & Lu, *Nuc. Acids Res.*, 19:4761–4766 (1981)), Deoxyinosine 3'-Endonuclease from *E. coli* (Yao et al., *J. Biol. Chem.* 270: 28609–16 (1995); Yao et al., *J. Biol. Chem.* 269: 31390–96 (1994)).

Another example of nucleic acid repair enzyme is an enzyme system comprising a glycosylase combined with an AP cleaving enzyme, such as endonuclease or lyase. Together glycosylase and AP cleaving enzyme, such as endonuclease or lyase cleave oligonucleotide probe/target polynucleotide duplex at a point of mismatch. A glycosylase creates an abasic sugar (an AP site) at the point of mismatch, which then is cleaved by an AP cleaving enzyme, such as endonuclease or lyase. Illustrative enzymes in these categories are detailed below.

glycosylases: tag-1, alkA, ung, fpy, mutY, nth, xthA, nfo, recj, uvtA, uvrD, mfd, mutH, mutL, muts, uracil DNA glycosylase, hydroxymethyluracil glycosylase, 5-mC DNA glycosylase, hypoxanthine DNA glycosylase, thymine mismatch DNA glycosylase, 3-mA DNA glycosylase, hydrated thymine DNA glycosylase (endonuclease III), pyrimidine dimer glycosylase These enzymes can come from any different biological sources. For example, Friedberg et al., DNA REPAIR AND MUTAGENESIS (ASM Press 1995), lists uracil DNA glycosylases from herpes simplex virus types 1 and 2, equine herpes virus, Varicella zoster virus, Epstein Barr virus, human cytomegalovirus, *Mycoplasma lactucae*, *E. coli*, *B. subtilis*, *M. luteus*, *B. steorophermaophilus*, *Thermothrix thirpara*, *S. pneumoniae*, *Dictyostelium discoideium*, *Artenia salina*, *S. cerevisae*, *Hordeum vulgare*, *Zea mays*, *Triticum vulgare*, rat liver mitochondria, calf thymus, human placenta, HeLa S3 cells, and acute leukemia blast cells.

AP cleaving enzymes: *E. coil* exonuclease III, *E. coli* endonuclease IV, Saccharomyes AP endonuclease, *Drosphila melanogaster* AP endonuclease I and II, human AP endonuclease, human AP lyase, BAP endonuclease, APEX endonuclease, HAP1 and AP endonuclease In addition to the above systems, cleavage may also be effected by using a glycosylase enzyme, as described above, in combination with basic conditions and increased temperature. In this embodiment, increasing pH and temperature effectuates cleavage at the AP site created by the glycosylase enzyme. Suitable parameters for cleavage of the AP site are pH levels of approximately 8 to 14, and temperatures ranging from approximately 50° to 95° C.

In another embodiment the present invention employs a nucleic acid repair enzyme that is thermally stable, in the sense that the enzyme would function at some elevated temperature, such as from 50° to 80° C. Additionally, it is preferable that the thermally stable nucleic acid repair enzyme withstand temperatures up to 100° C. for short periods.

For instance, the present invention contemplates the use of a thermally stable glycosylase. An example of a thermally stable glycosylase is the ORF10 protein encoded by the DNA sequence of FIG. 11. This enzyme has been synthesized by Richard P. Cunningham at the State University of New York at Albany, according to the methods of Example 13.

The substrate activity of the ORF10 enzyme includes both base cleaving properties and AP endonuclease activities. The AP endonuclease activities of this enzyme may be enhanced, however, by changing the amino acid residue in position 126 of FIG. 11 from a tyrosine to a lysine. This substitution may be achieved by site directed mutagenesis by the methods discussed in Deng, et al., *J.A. Anal. Biochem.* 200: 81 (1992).

The ORF10 glycosylase is a homologue of the endonuclease III family. As such, the skilled artisan may identify and isolate genes of the endonuclease III family from other thermophilic bacteria. Suitable probes may be designed as degenerate nucleotide coding sequences for the following amino acid sequences which are highly conserved amongst the members of the endonuclease III family: (SEQ ID NO:1), PYVILITEILLRRTT; (SEQ ID NO:2), AILD-LPGVGKYT; (SEQ ID NO:3), MVDANFVRVINR.

These degenerate oligonucleotides may be used as PCR primers to amplify portions of the gene from the chromosomal DNA of thermophilic bacteria by PCR. Such amplified PCR products may then be used to screen a library of the thermophilic bacterium. Positive clones would be sequenced and the coding sequence for the mismatch glycosylase cloned into an expression vector for protein production.

Additionally, the invention can utilize a combination of nucleic acid repair enzymes. For example, a nucleic acid repair enzyme can be used in combination with a AP cleaving enzyme. Advantageously, mutY is used in combination with AP cleaving enzymes, such as DNA lyase or DNA AP endonuclease. Such a system of enzymes enhances the speed at which cleavage occurs.

According to the present invention, moreover, the nucleic acid repair enzyme can be attached to a probe or a combination of probes. The attachment of the enzyme to a probe enhances the speed at which cleavage occurs by keeping the nucleic acid repair enzyme in proximity with the probe.

Pursuant to one aspect of the invention, the nucleic acid repair enzyme is a single enzyme that exhibits both glycosylase and AP cleaving properties, which can be attached to a single probe which hybridizes to the target polynucleotide at the site of a point mutation. This enzyme can be attached either to the 5' or to the 3' end of the probe. The attachment of the nucleic acid repair enzyme to the probe can be accomplished by linking methods described, for example, by Corey et al., *Science* 238:1401 (1987), and Corey et al., *J. Am. Chem. Soc.* 111:8523 (1989).

Figure 8:
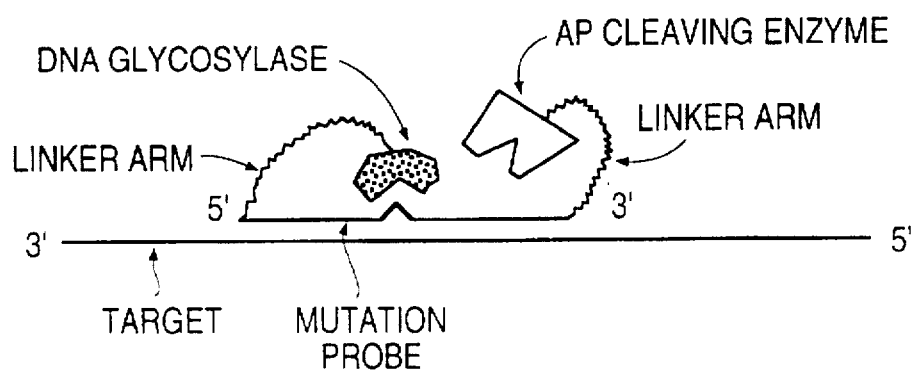
FIG. 8 is a schematic drawing showing the attachment of glycosylase and AP cleaving enzyme to the 5' and 3' ends of a mismatch probe.

In another embodiment, the nucleic acid repair enzyme is made up of two separate enzymes, as discussed above; one enzyme is a glycosylase and the other has AP cleaving properties. Such enzymes can be utilized so that the glycosylase is attached to one end of the probe and the AP cleaving enzyme to the opposite end (see FIG. 8).

Figure 6A:
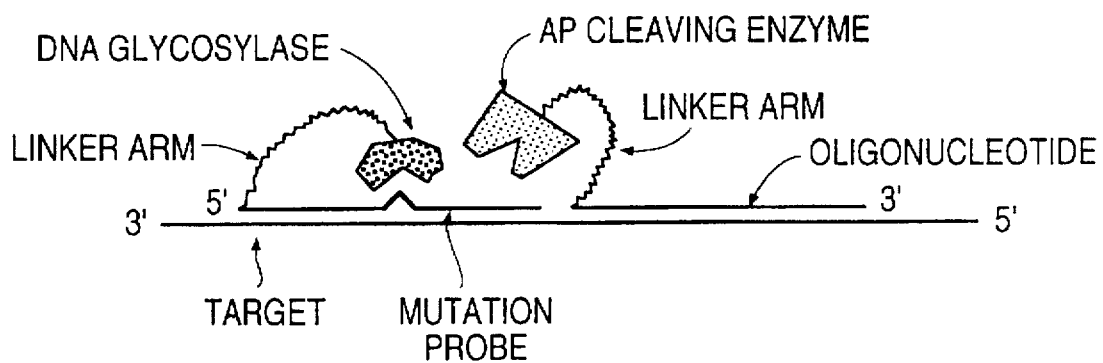
FIGS. 6A and B are schematic drawings showing the linking of nucleic acid repair enzyme to two separate probes designed to hybridize with a target polynucleotide. The nucleic acid repair enzyme comprises two separate individual enzymes, a glycosylase and an AP cleaving enzyme. The glycosylase is linked to a mismatch probe, i.e., a probe that is designed so that it will form a mismatch upon hybridization with the target polynucleotide. The AP cleaving enzyme is linked to a second probe which is complementary to the target polynucleotide and hybridizes to the target polynucleotide at a location adjacent to the mismatch probe.
Figure 6B:
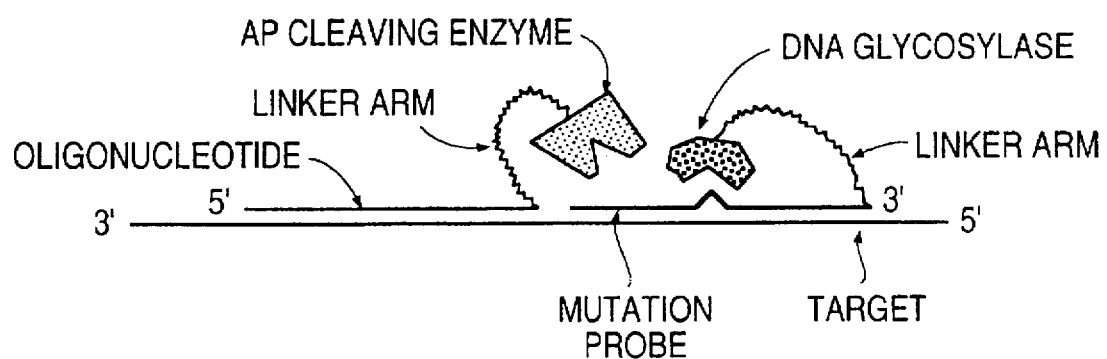

Another embodiment of the present invention employs two probes (see FIG. 6A and 6B). The first probe comports with the description above; that is, it is complementary to a non-mutated sequence in the target polynucleotide, so that a mismatch will occur at the site of point mutation in the target polynucleotide. The second probe is designed to hybridize to the target polynucleotide at a location adjacent to the first probe, i.e., at a location such that the second probe is close enough to the first probe so that enzyme attached to the former can effect cleavage of the latter. Preferably, the second probe will hybridize contiguously with the first probe, but the second probe also can hybridize between 0 and 5 base pairs from the first probe.

Figure 7:
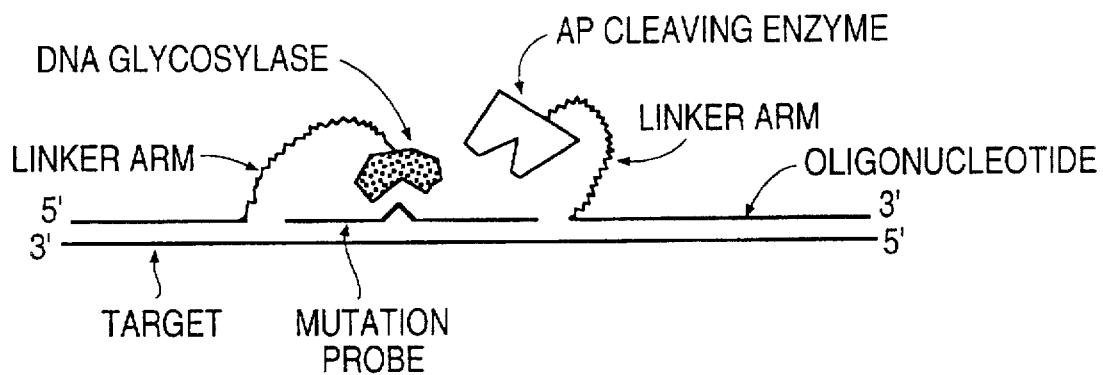
FIG. 7 is a schematic drawing depicting a mismatch probe used in combination with a second and third probe which hybridize to the target polynucleotide at a location adjacent to the mismatch probe. The glycosylase is attached to the 3' end of the second probe and the AP cleaving enzyme is attached to the 5' end of the third probe.

In another embodiment three probes are used (see FIG. 7). The first probe corresponds to the first probe described above, except that it is not attached to a glycosylase enzyme. Rather, the glycosylase and AP cleaving enzymes are attached to the second and third probes. These second and third probes are designed to hybridize to the target polynucleotide at a location adjacent to the first probe, as described above. Preferably, the second and third probe will hybridize contiguously with the first probe, but on opposite ends (see FIG. 7). The second and third probes, however, can hybridize between 0 and 5 base pairs from the first probe.

The present invention also provides for the detection of specific but unknown point mutations using a combination of different glycosylases. As described above, a first probe is designed complementary to a non-mutated sequence of the target polynucleotide. The first probe is then attached to a particular glycosylase enzyme.

For example, three different first sets of probes may be attached respectively to mutY, Thymine mismatch and All type mismatch enzyme. Each of these glycosylases will only perform its function, i.e., creating an abasic sugar, at the site of a particular point mutation. Respectively, mutY, Thymine mismatch and All type mismatch perform to create abasic sugars at A/G and A/C mismatches, G/T mismatches, and all mismatches.

Figure 9:
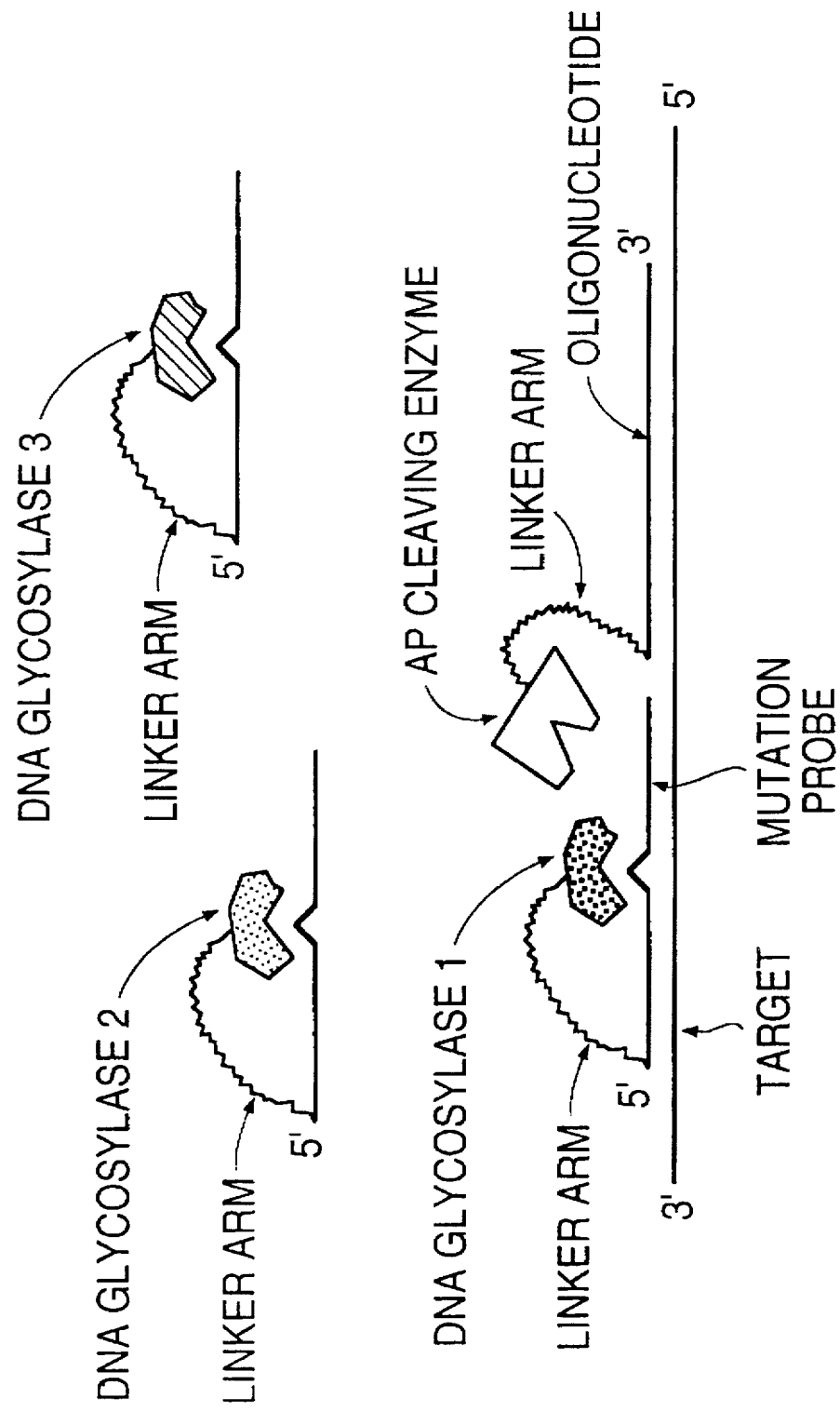
FIG. 9 is a schematic representation depicting the use of a combination of glycosylases to detect a point mutation. Three probes are depicted, and a different glycosylase is attached to each one. For a particular point mutation, only a specific probe or probes will be cleaved, thereby indicating the presence of the particular point mutation.

Therefore, only those probes forming mismatches corresponding with the attached glycosylase will be cleaved. A second probe with an attached AP cleaving enzyme can be combined with the first probe, as discussed above and shown in FIG. 9.

Detection of the cleaved probe can be achieved through the attachment of different flourophores at the 3' end of the probe molecule. That is, a different flourophore is associated with each different glycosylase. The presence of the particular flourophore may be detected by methods known to those skilled in the art.

In accordance with another aspect of the present invention, one can detect the existence of a specific but unknown point mutation. To this end, three probes are designed so that each probe contains a different base corresponding to the point in the target sequence where the point mutation is known to occur. Each of the three probes are specific lengths. Upon cleavage, the length of the cleaved molecule indicates the identity of the specific mismatch present in the target polynucleotide.

This approach also would allow for the identification of the relative amounts of mutated versus wild type target polynucleotides in a sample. One can measure the relative amounts of wild and mutated polynucleotide by assessing the relative amounts of cleaved probe.

Moreover, the present invention comprehends glycosylases having associated AP cleaving properties. For example, a mutY enzyme having both glycosylase and associated AP cleaving properties may be combined with a separate AP cleaving enzyme as contemplated above.

After cleavage by a nucleic acid repair enzyme, pursuant to the present invention, the amount of cleaved oligonucleotide probe can be determined. In particular, the amount of cleaved oligonucleotide probe can be quantified to indicate the amount in a given sample of target polynucleotide containing a point mutation. The size of the cleaved oligonucleotide probe indicates the site of the mismatch in the target sample.

One method of detecting the amount of cleaved oligonucleotide probe fragments and the size of cleaved oligonucleotide probe fragments is by gel electrophoresis. Radiolabeling, fluorescent labeling or other labeling of the synthetic oligonucleotides can be used, and the processed samples then are electrophoresed on a gel, typically a 20% polyacrylamide/7M urea-1×TBE gel.

The gel then can be autoradiographed. The autoradiograph can be scanned electronically, along with control lanes containing different amounts of radiolabeled material. The density of the uncleaved and cleaved oligonucleotide can then be interpolated from electronically scanned data and controls, and the amount of cleavage quantitated. A similar process can be used for florescence using a fluorimeter. Chemiluminescence can be detected by autoradiography.

Another method for detecting probe fragments involves capillary electrophoresis. By this approach, the processed samples are electrophoresed rapidly, allowing quantitation of the amount of cleaved oligonucleotide probe and size determination. Capillary electrophoresis is described in Guttman et al., *J. Chromatography* 593:297–303 (1992).

Yet another method entails the use of fluorescence resonance energy transfer (FRET), which can be used by placing two fluorescent molecules at either end of the synthetic oligonucleotide. When cleavage occurs, the two fluorescent molecules are physically separated, reducing florescence. Accordingly, reduced fluorescence indicates the amount of cleaved oligonucleotide probe.

In general, hybridization of a synthetic, single-stranded oligonucleotide probe to a single-stranded target polynucleotide occurs at a temperature roughly 3° C. per nucleotide at 1M salt conditions. For a 20-mer synthetic oligonucleotide, therefore, the hybridization temperature can be predicted to be about 60° C.

In the present embodiment, hybridization can be facilitated by a helix destabilizing molecule. For instance, a helix destabilizing molecule can allow hybridization of a 20-mer synthetic oligonucleotide to target polynucleotide at 40° C.

By reducing the temperature necessary to achieve hybridization of oligonucleotide probe to target polynucleotide, helix destabilizing molecule can eliminate the need for thermostable enzymes and expensive thermocyclers.

Exemplary helix-destabilizing molecules include *I, herpes simplex virus-type I ICP8, nucleolin, and adenovirus DNA-binding protein. See Topal & Sinha, *J. Biol. Chem.* 258(20): 12274–79 (1983); Alberts & Frey, *Nature* 227: 1313–18 (1970); Hosoda & Moise, *J. Biol. Chem.* 253(20): 7547–55 (1978); Ghisolfi et al., *loc. cit.*, 267(5): 2955–59 (1992); Boehmer & Lehman, *J. Virol.* 67(2): 711–15 (1993); Zijderveld & van der Vleit, *J. Virol.* 68(2): 1158–64 (1994); Monaghan et al., *Nucleic Acids Research* 22(5): 742–48 (1994).

When facilitated by helix-destabilizing molecule, hybridization in accordance with the present invention can be effected with long synthetic oligonucleotides, without the use of thermostable enzymes or expensive thermocyclers. A "long" oligonucleotide in this context is greater than 25 nucleotides but preferably not greater than 100 nucleotides. Use of such long oligonucleotides affords the advantage of hybridizing to the target polynucleotide with increased specificity.

The presence of a helix-destabilizing molecule thus allows for the use of long synthetic oligonucleotides, without thermostable enzymes or expensive thermocyclers. The helix-destabilizing molecule allows for the dispensation of thermostable enzymes because it lowers the temperature necessary for hybridization. In some instances, however, the helix-destabilizing molecule will not lower the temperature sufficiently to allow for the dispensation of thermal stable enzymes. In these instances, the present invention could, in principle employ a helix-destabilizing molecule that is thermally stable, in the sense that the enzyme would function at some elevated temperature, such as from 50° to 80° C. Additionally, the thermally stable enzyme would withstand temperatures up to 100° C. for short periods. No such thermostable helix-destabilizing molecule has been disclosed in publication to date, however. Accordingly, it is preferable that the destabilizing function of the enzyme employed in the invention should be effected in a temperature in the range of 40° to 70° C.

Detecting of point mutations, in accordance with the present embodiment, is useful in detecting diseases resulting from inherited genetic mutations. There are many well known examples of such diseases, including sickle cell anemia, and diseases resulting from the mutation of p53 cancer tumor suppressor gene, hypoxanthine phosphotransferase, and oncogenes. In each of these cases, the gene contains a detectable nucleotide or nucleotides that have been mutated to a different base. These point mutations cause the disease state in the individual.

Oscillation Reaction

In another embodiment of this invention, an oscillation reaction is created whereby the nucleic acid repair enzyme cleaves the oligonucleotide probe, and the shortened, cleaved oligonucleotide fragments dissociate from the target polynucleotide at a predetermined temperature. That is, The oligonucleotide probe is designed so that, at the predetermined temperature, the oligonucleotide fragments dissociate from the target polynucleotide after cleavage by nucleic acid repair enzyme. A cycle or oscillation reaction then occurs because the target polynucleotide hybridizes to another oligonucleotide probe, and the cleavage process is repeated.

As a consequence, a small number of target polynucleotides can be detected in a sample, since a single target polynucleotide catalyses the formation of a large number of oligonucleotide probe cleavage fragments. The oscillation reaction enables the detection of as little as one molecule of target polynucleotide in a sample. The oscillation reaction can detect from 10–100 target polynucleotide molecules in a sample. Theoretically, the oscillation reaction may detect as little as one target polynucleotide molecule in a sample.

To accommodate the oscillation reaction, a high concentration of oligonucleotide probe is utilized. In this regard, a suitable radiolabeled probe concentration is from 0.01 to 10 pmol. Other concentrations can be used depending on the desired length of autoradiograph exposure times.

One of skill in the art can refer to Duck et al., *BioTechniques* 9(2): 142 (1990), which refers to CPT a similar but less advantageous technique for amplifying probe.

Preferably, the oscillating reaction is performed at a isothermal temperature of 3N—20° C., here N is the length of the probe in base pairs. Within this working range the optimal temperature is determined empirically. Preferably, the reaction is performed with 0.01 to 10 pmol of labeled probe, in the presence of either synthetic target sequence or DNA purified from a sample source. This target DNA will ranges from 1 to $10^{12}$ molecules.

To reduce the double stranded nature of the target DNA the DNA can be partially degraded with DNAse I to form shorter DNA fragments. The reaction can also be performed in the presence of 10 to 100 pmol of a helix destabilizing molecule in the presence of 5 to 10 mM $Mg^{-2}$. With the helix destabilizing molecule the operating temperature will need to be empirically determined.

A typical reaction is performed in a buffer composed of 20 mM Tris-HCL, pH 7.6, 80 mM NaCl, 1 mM dithioerythritol, 1 mM EDTA, pH 8.0, with 5 to 50 units of mutY enzyme. The reaction is allowed to proceed for 20 to 60 minutes, a loading dye of 98% formamide, 10 mM EDTA, pH 8.0, 0.025% xylene Cyanol FF, 0.025% Bromophenol blue is added to stop the reaction. The sample is then loaded onto a 20% polyacrylamide/7M urea 1×TBE gel and electrophoresed about 10 to 15 cm at 200 to 500 V. The gel is then autoradiographed for 1 minute to 5 days, dependent on the amount and specific activity of the probe, which is prepared by standard kinasing reaction conditions for T4 polynucleotide kinase.

Labeled Tail

In another embodiment of the present invention, the detection of cleaved oligonucleotide fragment is enhanced by the addition of a labeled tail. To add a labeled tail to a cleaved oligonucleotide fragment, an oligonucleotide probe can be synthesized so that it forms a mismatch when hybridized to target polynucleotide. The oligonucleotide probe can contain a protected 3' group, preventing a polymerase from extending from the probe sequence. The probe then can be cleaved by a nucleic acid repair enzyme.

Figure 2:
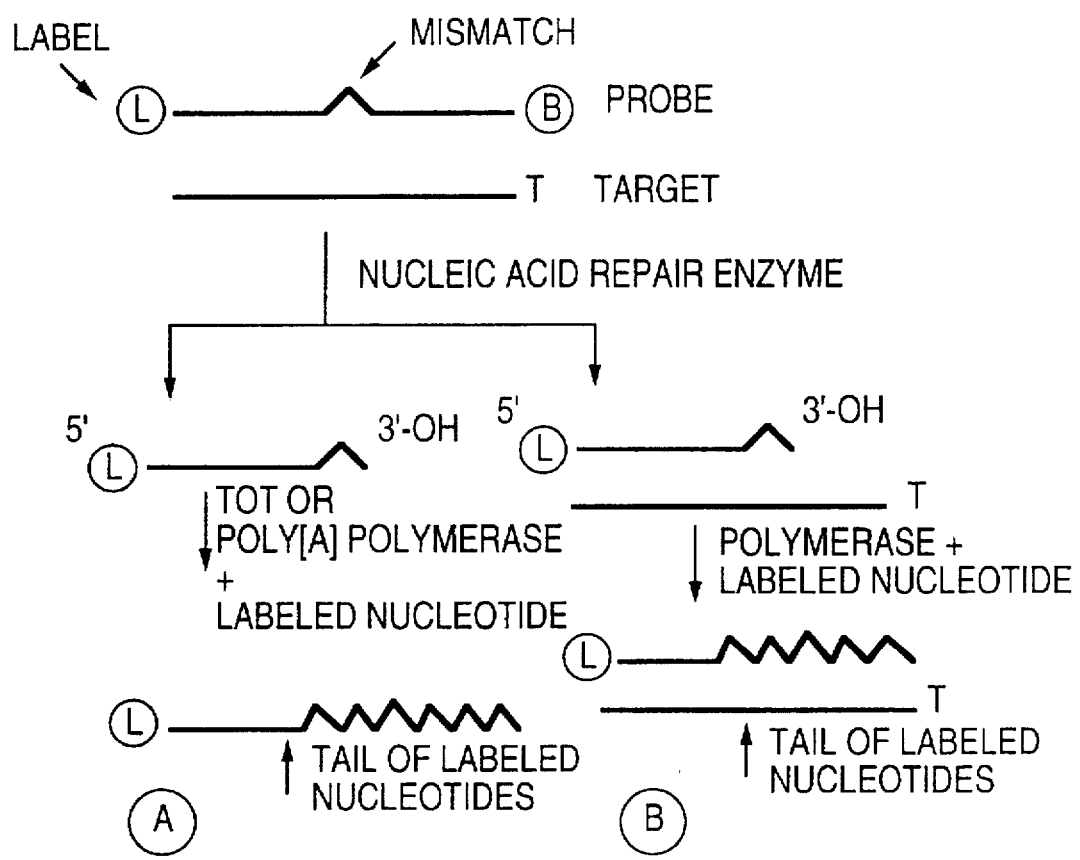
FIG. 2 is a schematic drawing showing the tail labeling of cleaved probe. Probe is cleaved at the site of mismatch. If the probe is designed to dissociate, as shown in part A, it can, after dissociation, be tagged with a labeled nucleotide tail. If the probe is designed to remain hybridized to target after cleavage, as shown in part B, then it can also be tagged with a labeled nucleotide tail.

In one aspect of the present embodiment, represented by side B of FIG. 2, the 5' region of the probe can be designed so that it is long enough to remain bound to the target sequence when the mismatch is cleaved. The 3' region of the probe can be designed so that it is short enough so that upon cleavage it dissociate from the target polynucleotide.

The 5' region of the probe that upon cleavage has remained bound to the target polynucleotide now can form a template for DNA polymerase with appropriate dNTPs, as shown in side B of FIG. 2.

If the nucleotides used in this embodiment are labeled with a radionucleotide or with some other marker, such as a fluorescent label, then the amount of cleavage can be assayed, using these labeled nucleotides as the signal.

In another aspect of the present embodiment, the 5' region is so designed that it dissociates from the target polynucleotide when the mismatch is cleaved, as shown in side A of FIG. 2. The 5' cleavage fragment then can be extended with polyA polymerase or terminal deoxynucleotidyl transferase (TdT), as shown in side A of FIG. 2, and detected.

For example, if the tails consist of polymers of adenosines, the tails will hybridize to polymers of oligonucleotide composed of thymines. If the nucleotides used in this polyA polymerase or TdT reaction are labeled with a radionucleotide or with some other marker, such as a fluorescent label, then the amount of cleavage can be assayed, using these labeled nucleotides as the signal.

Additionally, the oligonucleotide probe described in the previous two aspects of the present embodiment can have another feature, a ligand type molecule at the 5' end of the probe oligonucleotide. The ligand can serve to label the probe. The ligand can be a biotin group, or a group extendable with poly (ADP) ribose polymerase. Additionally, the ligand can be DNP (dinitrophenol) or cholesterol moieties.

By attaching a ligand molecule to the 5' end of the probe oligonucleotide, molecules that bind to the ligands, such as antibodies can be used to affinity purify the newly formed tails. For example, after cleavage the probes with a biotin ligand can be passed over an avidin or streptavidin column. The probes with a poly(ADP)ribose ligand can be passed over a antipoly(ADP)ribose column. The DNP and cholesterol moieties can be passed over column with antibody against DNP and cholesterol, respectively. Affinity purification techniques, including affinity chromatography are well known to those skilled in the art.

Detecting Known Sequences

Yet another embodiment of this invention provides for detecting, identifying, measuring, or localizing, inter alia, known sequences in a target polynucleotide in a biological sample. This aspect of the invention includes hybridizing a single-stranded oligonucleotide probe to a target polynucleotide to form a hybrid double-stranded polynucleotide. In this embodiment, the probe is designed so that it includes a mismatched or repairable base sequence.

Because the probe so designed is not complementary to the target polynucleotide, there is a mismatch between the probe containing a synthesized mutation or mismatch site and the wild-type target polynucleotide. The mismatch occurs at the site of a mismatched or repairable base sequence.

The probe is cleaved at the point of mismatch with a nucleic acid repair enzyme as mentioned above. The cleaved polynucleotide fragments are then detected as mentioned above.

An example of the present embodiment is as follows. The probe oligonucleotide can be synthesized so that it is complementary to the target polynucleotide sequence except at a single nucleotide, which is chosen to be near the middle of the probe. The wild-type probe contains a cytosine base in the middle of the probe that correctly hybridizes to a guanosine base on a wild-type target polynucleotide sequence. The mismatched probe can be designed by synthesizing an oligonucleotide probe wherein the cytosine base is replaced by an adenine base. The adenine base of the probe oligonucleotide mismatches to a guanosine base in the target molecule. But the rest of the strands of the probe and target are complementary. When treated with mutY, the probe are cleaved if it has hybridized to a non-mutated wild-type target polynucleotide.

If, however, the target polynucleotide contains a point mutation, so that the aforementioned target guanosine is in fact a thymine, the probe containing a mutation will not be cleaved. This is true because a mismatch will not have occurred, the probe adenine being complementary to the target thymine.

Another aspect of the present embodiment includes two probes, used independently, which contain mismatches at slightly different sites. Cleavage occurring for both probes in separate reactions confirms the presence of the target polynucleotide.

The present embodiment can utilize helix destabilizing molecules, as discussed above. Additionally, this embodiment can be performed using the oscillating and tailing methods already described. Moreover, this embodiment may employ the linking methods and use of a combination of glycosylases and either AP endocuncleases or AP lyases, as described above.

The present embodiment is useful in DNA diagnostics and DNA profiling.

Detecting the Repair Index in a Sample

Yet another embodiment of the present invention comprehends detecting the repair index of a mismatched or damaged oligonucleotide probe. The "repair index" in this regard is defined as the ratio of the amount of cleavage in a sample mixed with base-repairing enzyme (shown in the right side of FIG. 3) to the amount of cleavage in a sample of control, which contains no base-repairing enzymes (control shown in FIG. 3 on left side).

The repair index indicates the extent to which base-repairing enzymes have repaired a sample of mismatched or damaged oligonucleotide probes. A "base-repairing enzyme" is one that effects repair of a mismatched probe sequence that has hybridized to a target polynucleotide. The base-repairing enzyme replaces the mismatched base with a base that is complementary to the target polynucleotide. Examples of base-repairing enzymes are E.coli DNA purine transferase (E.C. 2.6.99.1), human $O^6$-methylguanine-DNA methyltransferase (Koike et al. *J. Biol. Chem.* 265: 14754) and E. coli DNA photolyase (EMBL Data Library Accession Number S32737).

Figure 3:
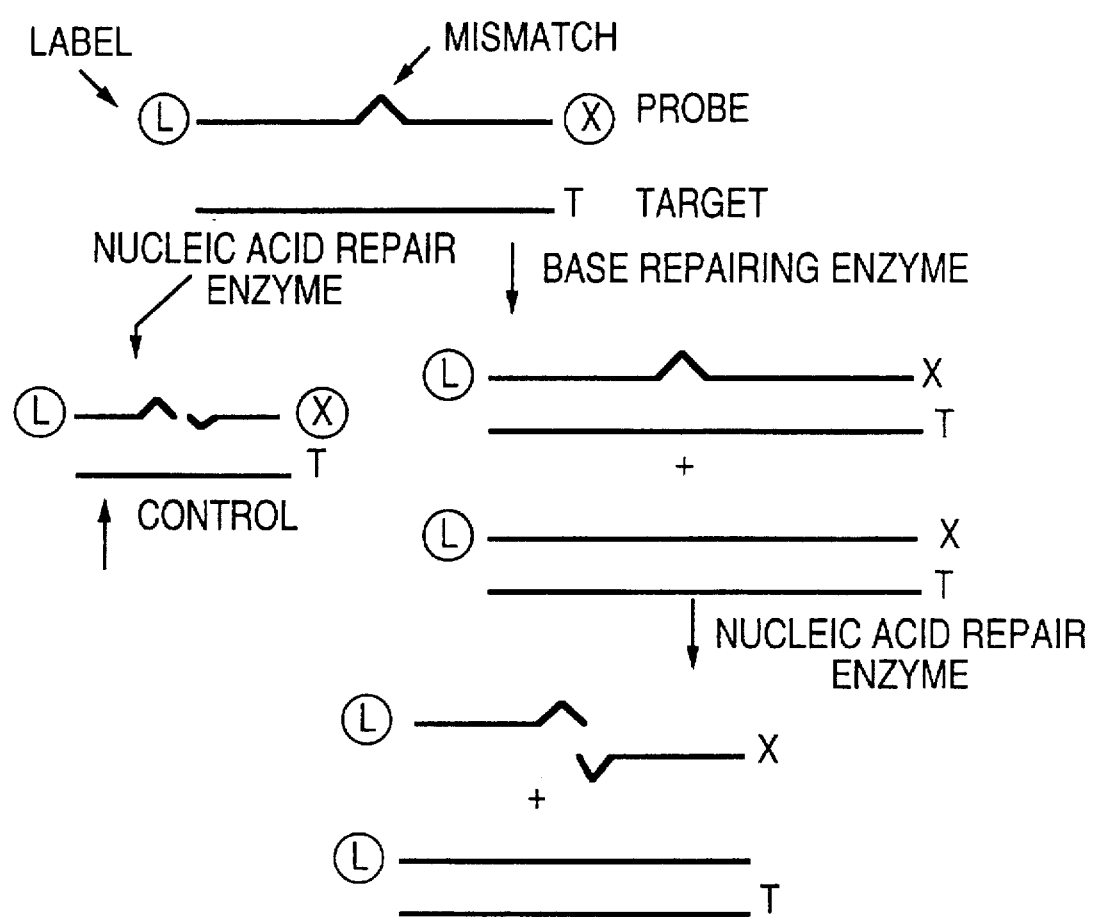
FIG. 3 is a schematic drawing showing the detection of the index of repair of a mutated or damaged probe. Probe is hybridized to target and then base-repairing enzyme is added. Next, nucleic acid repair enzyme is added and cleaves those probes which have not been repaired. A control group is shown on the left side of the figure.
Figure 4:
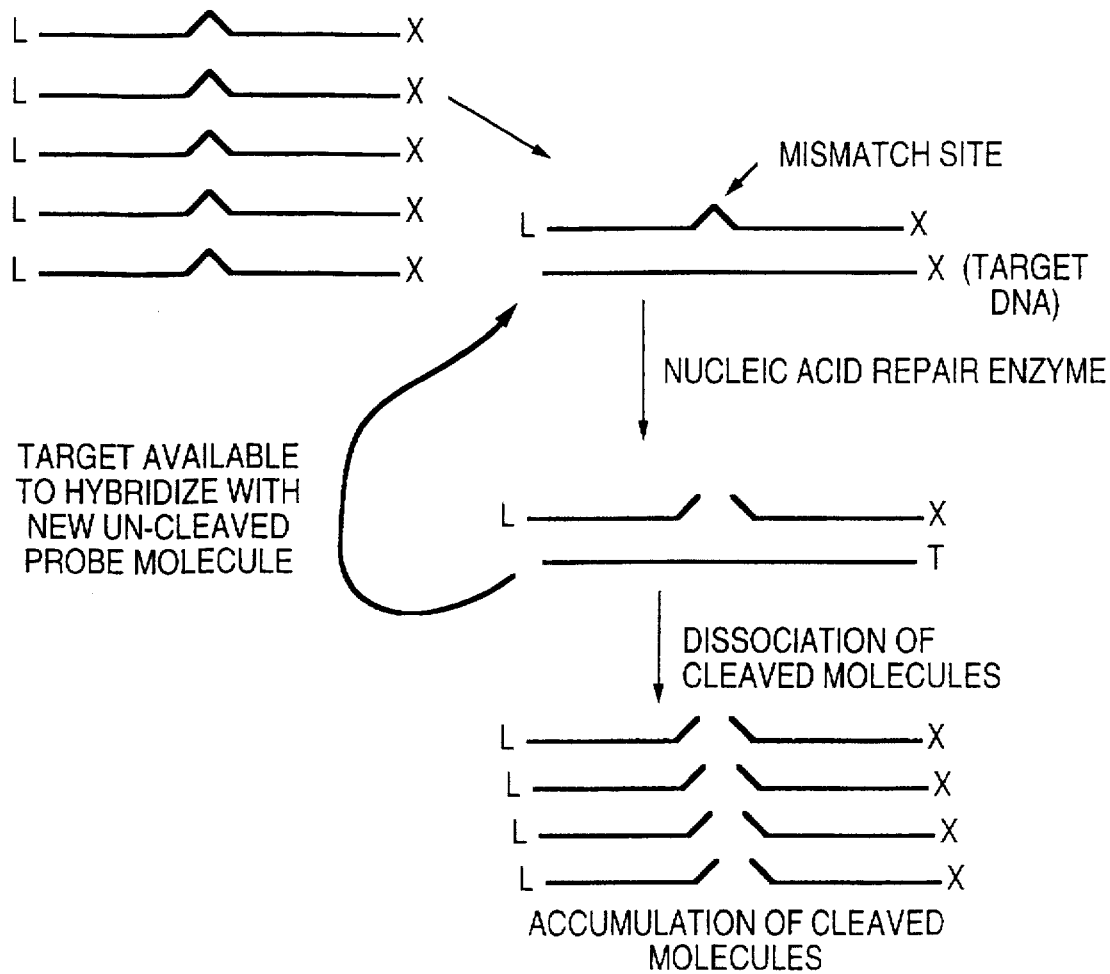
FIG. 4 is a schematic drawing showing the oscillating reaction. An excess of mismatch probe hybridize to available target molecules in the reaction mixture, wherein a Nucleic Acid Repair Enzyme cleaves at the mismatch site. The probe molecule is designed so that the shorter cleaved molecules dissociate from the target molecule. The target then hybridizes to a new intact probe molecule, generating the oscillating reaction. The accumulation of cleaved molecules is linear with the amount of target molecules available.

The embodiment depicted in FIG. 3 involves hybridizing a single-stranded oligonucleotide probe to a target polynucleotide to form a hybrid double-stranded polynucleotide. The probe is designed so that it includes a mismatched or a repairable base sequence. Such a probe can be designed according to the methods described above.

Because probe so designed will not be complementary to the target polynucleotide, there will be a mismatch between the mutated probe and the wild-type target polynucleotide. The mismatch will occur at the site of the mismatched or repairable base sequence.

Next, the hybrid double-stranded polynucleotide will be exposed to a base-repairing enzyme, which is defined above. The base-repairing enzyme will repair a certain amount of the mismatched or repairable base sequences, depending on the type of base-repairing enzymes employed.

The hybrid double-stranded polynucleotide then will be exposed to a nucleic acid repair enzyme, which cleaves non-repaired probe at the point of mismatch. The cleaved nucleotide fragments can then be detected by the methods described above.

To obtain the repair index, as defined above, the amount of cleavage in a sample mixed with base-repairing enzyme is compared to the amount of cleavage in a sample of unrepaired control.

Determining the repair index is useful in determining the potency of cancer therapeutic agents on an individual. For example, an oligonucleotide is synthesized with a base that has been modified to contain a base adduct. Several base adducts are known to be the result of certain chemotherapeutic drugs. See Friedman et al., *supra*, table 5-3. Base adducts cause a significant distortion of the DNA helix and are both repairable by base repair enzymes and cleaved by nucleic acid repair enzymes.

Next, the probe is hybridized with target polynucleotide in a medium containing the base-repairing enzymes of a particular individual, and then the duplex is exposed to nucleic acid repair enzyme. Accordingly, the index of repair indicates the extent to which the individual would repair mutations that would be induced by a particular cancer therapeutic agent.

The present embodiment can employ helix destabilizing molecules as described above. Additionally, this embodiment of the invention can be performed using the oscillating and tailing methods described above. Moreover, this embodiment may employ the linking methods and use of a combination of glycosylases, as described above.

Probe Directed in Vitro Mutagenesis

Yet another embodiment of the present invention comprehends modifying a single base in a target polynucleotide.

This aspect of the invention includes hybridizing a single-stranded probe to a circular single-stranded target polynucleotide. The probe is constructed so that it contains a single base that will form a mismatch with the target polynucleotide at a predetermined site. The probe is designed to contain fewer base sequences than the target polynucleotide so that hybridization results in a partially double-stranded circular nucleic acid molecule (See FIG. 5).

This embodiment of the present invention comprehends a probe which can be either an oligonucleotide molecule or a peptide nucleic acid molecule. Where the probe is an oligonucleotide molecule, the partially double-stranded construct, described above, is converted into a completely double-stranded construct by filling in the single-stranded region of the probe-target hybrid (see FIG. 5). This conversion can be accomplished using DNA Polymerase and Ligase according to the methods employed by M. Smith and S. Gilliam (1981), in 3 GENETIC ENGINEERING 1 (J. K. Setlow & A. Hollaender, eds.). Preferably, the partially double-stranded construct is treated with T4 or T7 DNA polymerases and T7 or T4 DNA lygases. These polymerase enzymes are superior because they lack 5' to 3' exonuclease activity. Additionally, these enzymes will not effect strand displacement of the oligonucleotide probe. Accordingly a completely double-stranded construct will be formed containing the original probe base sequences.

Figure 5:
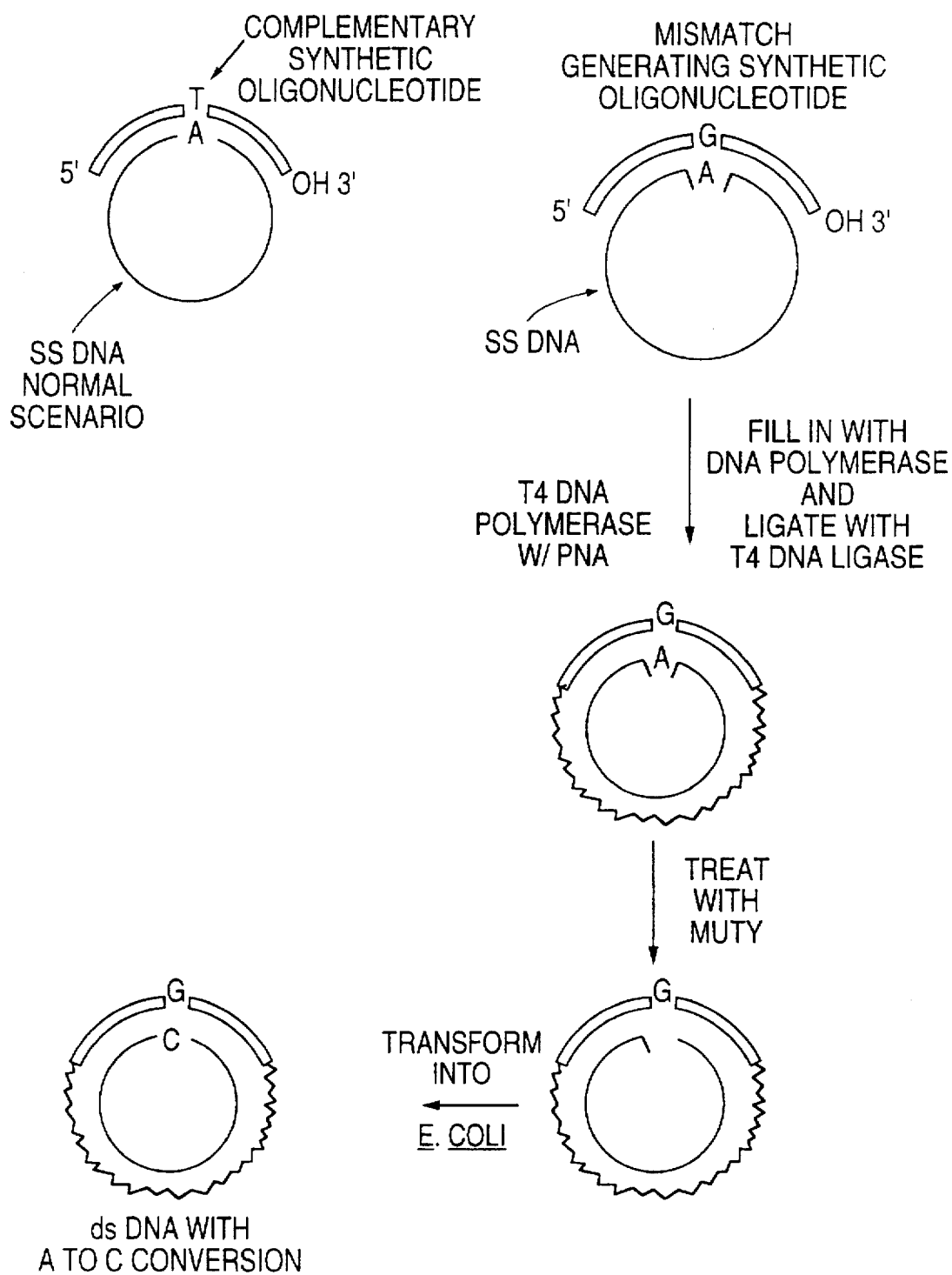
FIG. 5 is a schematic drawing showing an oligonucleotide directed in vitro mutagenesis reaction. A probe is hybridized to single stranded DNA (ssDNA) generating a mismatch in the ssDNA. A new strand of DNA is synthesized in vitro with DNA polymerase and ligase, generating a double stranded DNA (dsDNA) molecule. This dsDNA molecule is treated with mutY, cleaving and removing the mismatched base. The cleaved dsDNA molecule is transformed into *E. coli*, and the replicated dsDNA molecule then has a different base at the site of the mismatch.

This fully double-stranded molecule is then treated with a nucleic acid repair enzyme which cleaves the target polynucleotide strand at the point of mismatch, creating a gap in the target polynucleotide (see FIG. 5). Next, the probe-target hybrid is transformed into a bacteria according to techniques well known to those skilled in the art. In the process of transformation, the gap created by cleavage is filled with base(s) complementary to exposed probe bases.

Where the probe is a peptide nucleic acid molecule ("PNA"), a different methodology is employed. PNA's as contemplated in the instant invention are molecules containing neutral, peptide-like backbones and nucleobases. PNAs allow for the hybridization to RNA and DNA with higher affinity and specificity than conventional oligonucleotides. PNAs are commercially available, for example, from Per-Spective Biosystems, Inc. (Framingham, Mass.), and are described in Wittung et al., *Nature* 368, 561–563 (1994); Hanvey, et al., *Science* 258: 1481–85 (1992).

In the PNA probe method, a partially double-stranded probe target construct is formed, as discussed above. Next, a nucleic repair enzyme effects cleavage of the target polynucleotide at the point of mismatch. Because of its peptide-like backbone, the PNA probe is impervious to cleavage by a nucleic acid repair enzyme. Accordingly, the PNA probe is advantageous in that it assures that cleavage will not occur in the probe molecule at the point of mismatch. Instead, the nucleic repair enzyme will only be able to effect cleavage in the target polynucleotide.

Figure 10:
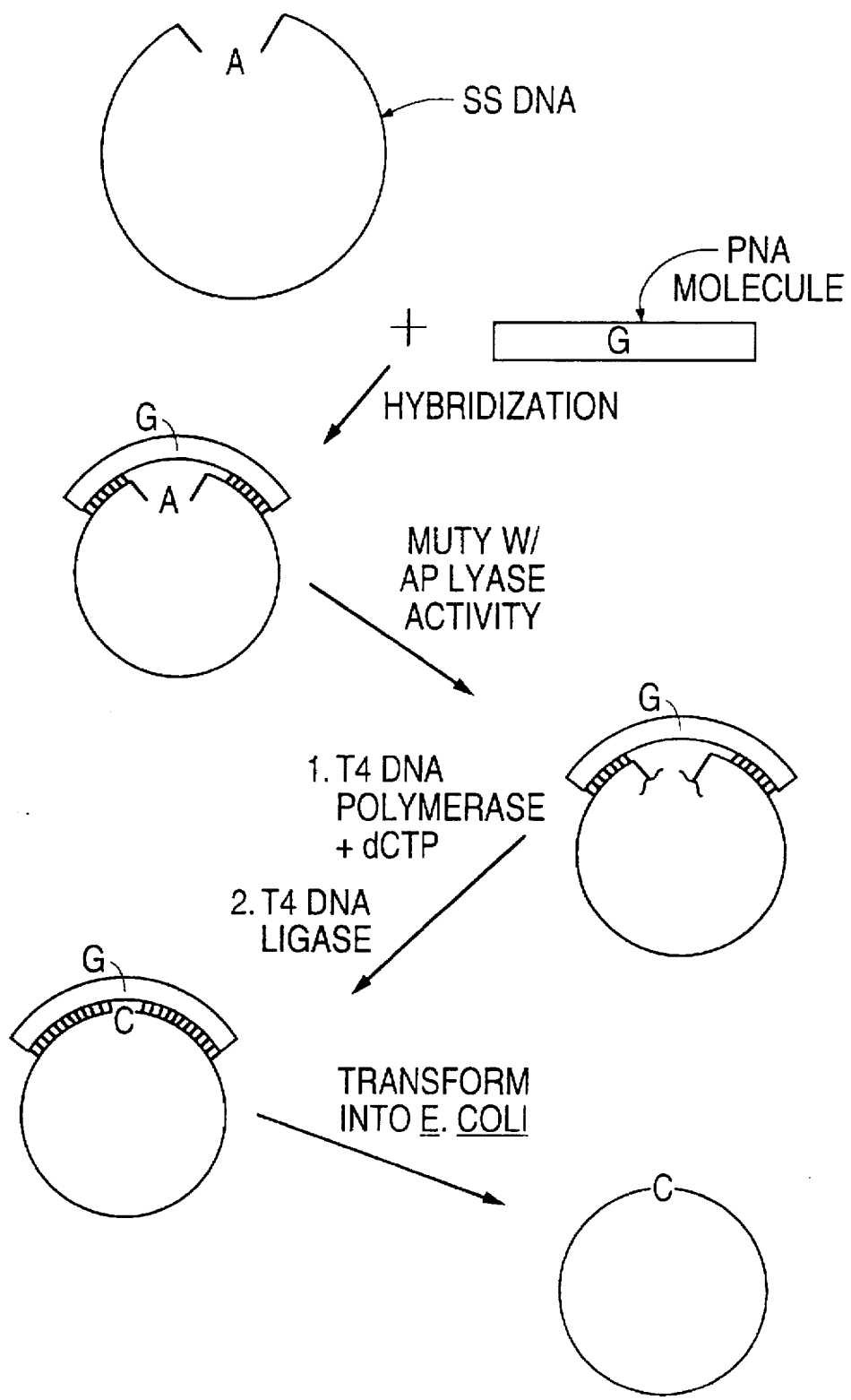
FIG. 10 is a schematic illustration of peptide nucleic acid ("PNA") directed in vitro mutagenesis. A PNA probe is hybridized to a single-stranded target polynucleotide, generating a mismatch. A nucleic acid repair enzyme is then contacted with the probe target hybrid cleaving the target strand at the point of mismatch. Next, the gap resulting from this cleavage is filled by contacting the probe target hybrid with appropriate polymerase enzymes.

The gap resulting from this cleavage can then be filled in with DNA polymerase and ligase in combination with the desired dNTP's (see FIG. 10). As discussed above, T4 DNA polymerase, T7 DNA polymerase, T4 DNA ligase, and T7 DNA ligase are preferred enzymes for this reaction. Additionally, other enzymes can be used to fill the gap in the target polynucleotide without causing strand displacement. In particular, Klenow fragment of DNA polymerase I may be used as described by Kunkel, T.A. *Nucleic Acids Mol. Biol.* 12: 124 (1988); *Proc. Natl. Acad. Sci. U.S.A.* 82: 488 (1985).

Next, the target polynucleotide strand can be separated from the PNA probe by heating the PNA-target hybrid to dissociate the two from each other. The temperature for disassociation is approximately 3° C. per mer in the PNA probe molecule plus approximately 20°C. as described in Wittung et al., *Nature* 368, 561–563 (1994). The target polynucleotide can then be purified by column size exclusion chromatography (e.g. G-SO) to obtain target that is free of PNA probe molecules.

The target polynucleotide may then be transformed into a bacteria as a single-stranded circular construct. Alternatively, the skilled artisan may obtain a double stranded construct by use of a primer, polymerase, ligase enzymes and dNTP's. A double-stranded construct may be advantageous because double-stranded circular polynucleotides generally transform with higher efficiency than single-stranded molecules.

The following examples merely illustrate the invention and, as such, are not to be considered as limiting the invention set forth in the claims.

EXAMPLE 1

Detection of Point Mutation Using the Oscillation Reaction

The enzyme mutY was purified by the method of Wu et al., *Proc. Nat'l Acad. Sci. USA* 89: 8779–83 (1992), to a concentration of about 50 units·$\mu l^{-1}$ from an overexpressed *E. coli* clone. (One unit is defined as the conversion of 1 fmol A/G mismatch synthetic oligonucleotide converted to nicked substrate per minute.) Two synthetic oligodeoxyribonucleotides were synthesized by standard phosphoramidite chemistries with the following sequences:

Oligonucleotide #1 (SEQ ID NO:4): 5'-CCGAGGAATTAGCCTTCTG-3'

Oligonucleotide #2 (SEQ ID NO:5): 5'-GCAGAAGGCGAATTCCTCG-3'

The oligonucleotides were purified on 20% polyacrylamide/7M Urea 1×TBE gels to about 95% homogeneity. The fragment was detected by autoradiography and a band cut from the gel. It was eluted from the gel slice by electrophoresis onto NA-45 paper (Schleicher & Schuler, Inc) by band interception, followed by elution from the paper by heating at 65° C. for 5 minutes in 2M TEAA (triethylammonium acetate). The sample was dried in a vacuum centrifuge until all solvent was removed.

Oligonucleotide #1 (Oligo 1 (SEQ ID NO:4)) was radiolabeled to high specific activity with about 60 pmols (0.1 mCi; 6000 Ci· mMol$^{-1}$) 32P-gamma-ATP and 100 units of T4 polynucleotide kinase at 37° C. for 1 hour. The radiolabeled fragment was further gel purified, as described above.

Oligonucleotide #2 (Oligo 2 (SEQ ID NO:5)) was diluted from 1 pmol·$\mu l^{-1}$ to $10^{-9}$ pmol·$\mu l^{-1}$ in sterile deionized water.

A typical reaction mix was set up that contained about 0.2 pmol of radiolabeled oligo 1, mutY buffer (20 mM Tris-HCl, pH 7.6, 80 mM NaCl, 1 mM dithioerythritol, 1 mM EDTA, pH 8.0, 3% glycerol; final concentration), 50 units of mutY enzyme, some reactions contained a dilution of Oligo 2 from 1 to $10^{-9}$ pmol. The final volume was 10 µl. The reaction proceeded at 37° C. for 60 minutes. The reaction was stopped by the addition of 1 µl of loading buffer (98% Formamide, 10 mM EDTA, pH 8.0, 0.025% Xylene Cyanol FF, 0.025% Bromophenol Blue). The reaction was electrophoresed on a 20% polyacrylamide/7M Urea 1×TBE gel, then autoradiographed. Lane 1 contains no target molecule. Lanes 2 to 11 contain $10^0$, $10^{-1}$, $10^{-2}$, $10^{-3}$, $10^{-4}$, $10^{-5}$, $10^{-6}$, $10^{-7}$, $10^{-8}$, $10^{-9}$ pmol of target. The cleavage from the reaction was detected by the generation of a smaller cleaved synthetic oligonucleotide fragment found in lanes 2 to 4. The truncated shorter molecule was due to cleavage at the A IG mismatch by the mutY enzyme.

EXAMPLE 2

Detecting Mismatches Using the Oscillation Reaction and Helix Destabilizing Molecule The nucleic acid repair enzyme mutY and the helix destabilization enzyme *I were used along with three synthetic oligonucleotides having the sequences:

(1) 5'-CCGAGGAATTAGCCTTCTG-3' (SEQ ID NO:6) Probe Mismatch (2) 5'-CCGAGGAATTCGCCTTCTG-3' (SEQ ID NO:7) Probe Wild-Type (3) 5'-GCAGAAGGCGAATTCCTCG-3' (SEQ ID NO:8) Target Probes 2 and 3 (SEQ ID NOS: 7 and 8, respectively) are complementary. Probes 1 and 3 (SEQ ID NOS:6 and 8, respectively) are complementary with a single base mismatch. The three DNA synthetic oligonucleotides were used as is or were radiolabeled with $^{32}$P-γ-ATP via T4 polynucleotide kinase.

Reactions were set up as indicated below with combinations of radiolabeled or cold oligonucleotides 1, 2 and 3(SEQ ID NOS: 6–8), with or without mutY and or *L Lanes 1 to 20 contained radiolabeled oligonucleotide 1 (SEQ ID NO:6). Lanes 3 and 4 contained radiolabeled oligonucleotide 2 (SEQ ID NO:7). Lanes 5 to 7 contained radiolabeled oligonucleotide 3 (SEQ ID NO:8). Lane 6 contained 10 pmols of cold oligonucleotide 1 (SEQ ID NO:6). Lane 7 contained 10 pmols of cold oligonucleotide 2 (SEQ ID NO:7). Lanes 2, 4, 9 and 16 contained 10 pmols of cold oligonucleotide 3 (SEQ ID NO:8). Lanes 10 and 17, Lanes 11 and 18, Lanes 12 and 19, Lanes 13 and 20, Lane 14 contained 1, 0.1, 0.01, 0.001, 0.0001, respectively of cold oligonucleotide 3 (SEQ ID NO:8). Lanes 2, 4, 6 to 20 contained mutY enzyme. Lanes 15 to 20 contained *L The reactions were setup with standard mutY reaction buffer and allowed to proceed for 1 hour at 37° C. The reactions were stopped, loading dye was added, and the material was run on a 20% polyacrylamide/7M Urea gel (1×TBE).

This experiment showed that the wild-type probe (SEQ ID NO:7) showed no cleavage. The probe with a mismatch (SEQ ID NO:6) showed cleavage. The presence of *I enhanced the rate of cleavage.

Only lanes 2, 9–14 and 16–20 showed any level of cleaved molecules dependent on target concentration.

This showed that only the mismatch probe (SEQ ID NO:6) cleaves when hybridized to its target sequence. The target was not cleaved in this reaction with either the mismatch (SEQ ID NO:6)(lane 6) or wild-type probe (SEQ ID NO:7) (lane 7). Further, the wild-type probe (SEQ ID NO:7) was not cleaved with mutY(lane 4).

EXAMPLE 3

Oscillating Reaction

In a hybridization reaction, a synthetic oligonucleotide of length N nucleotides has a temperature of hybridization (melting temperature or Im, in °C.) equal to 3N. For example, a synthetic oligonucleotide of 20 nucleotides has a temperature of hybridization of about 60° C. A shorter synthetic oligonucleotide of 10 nucleotides has a temperature of hybridization of about 30° C. At a set temperature, such as 45° C., the long 20-mer synthetic oligonucleotide hybridizes but the shorter 10-mer synthetic oligonucleotide does not.

The longer synthetic oligonucleotide hybridizes to a target sequence, then when it is cleaved at a specific place where a mismatch occurs two or more shorter synthetic oligonucleotides are be generated, which have lower thermodynamic stability. These shortened cleaved oligonucleotides dissociate from the target sequence, making it available for another hybridization event with the longer synthetic oligonucleotide. By using a high concentration of the longer original synthetic oligonucleotide probe sequence (mutation probe) the hybridization kinetics favors better, faster hybridization. Further, this allows the detection of a hybridization event by the accumulation of the shortened oligonucleotide fragments.

EXAMPLE 4

Helix Destabilization

A helix destabilizing molecule can also be added to the system of Example 3. In Example 3 the operating temperature is 45° C. and is kept at that temperature for this example. In a mode where a helix destabilizing molecule functions to reduce the hybridization temperature, the longer 20-mer synthetic oligonucleotide hybridizes not at 60° C., but rather at a lower temperature, for example, 48° C. At this temperature the hybridization temperature and the operating temperature are closer. This allows in one scenario the reduction of the operating temperature to a lower temperature, perhaps 37° C. Under this situation, mesophilic enzymes (those that function around 37° C.) can be used in the reaction. The practice of this example at such a temperature is advantageous in that it does not require thermophilic enzymes (those that function at high temperature extremes, e.g. 60°–70° C., and can withstand near boiling temperatures).

EXAMPLE 5

Oligonucleotide Directed in Vitro Mutagenesis

For modifying and generating new genetic sequences, in vitro mutagenesis is used. The earliest method of in vitro mutagenesis is that of M. Smith and S. Gilliam (1981), in 3 GENETIC ENGINEERING 1 (J.K. Setlow & A. Hollaender, eds.).

The nucleic acid repair enzymes can be used for oligonucleotide directed in vitro mutagenesis. For this example, the mutY is used as the example nucleic acid repair enzyme, however, other enzymes can also be used.

Single stranded DNA containing the cloned gene sequence to be modified can be generated by the method of inder & Boeke, Gene 19: 1–10 (1982), using the M13 bacteriophage system. A synthetic oligonucleotide is designed, which is complementary to the region to be modified with a Guanine mismatch at a position where the adenine is to be changed to a Cytosine (FIG. 5). The oligonucleotide is hybridized to the single stranded DNA, treated with T4 DNA polymerase and T4 DNA ligase by methods used by Smith (1981). The newly synthesized double stranded molecule with a single mismatch is then treated with 50 units of mutY in mutY buffer (20 mM Tris-HCl, pH 7.6, 80 mM NaCl, 1 mM dithioerythritol, 1 mM EDTA, pH 8.0) for one hour at 37° C. The material that is cleaved at the mismatch site is transformed into E. coli using methods well known to those skilled in the art. The transformants then are enriched for sequences containing the conversion of the adenine to the cytosine base pair.

EXAMPLE 6

Attachment of Glycosylase with Associated AP Endonuclease to the 5' End of an Oligonucleotide A synthetic oligonucleotide complementary to a region of the p53 gene is synthesized using standard phosphoramidite chemistry. Purified mutant *E. coli* mutY mismatch enzyme (with associated AP endonuclease) is linked to the 5' end of the oligonucleotide with linker using methods already described (Corey et al., 1987, Science, vol 238: 1401; Corey et al., 1989, Journal of the American Chemical Society, vol 111:8523). This forms a covalent linkage of an oligonucleotide of specific sequence, with a linker region covalently linked to *E. coli* mutY mismatch enzyme. The oligonucleotide is radiolabeled at the 3' end using poly (A) polymerase and $^{32}$P-cordycepin. As a comparison, oligonucleotides without enzymes are prepared and treated alongside with the enzyme linked oligonucleotides.

Using chromosomal DNA prepared from ML-1 myeloid leukemia cells, dilutions of the target DNA from $10^{-1}$ to $10^{-8}$ pmol are setup. To these tubes 10 pmols of radiolabeled probe, 100 ng of purified *E. coli* mutY mismatch enzyme for the unlinked oligonucleotide and buffer are added. The reaction was allowed to precede for 30 minutes at 37° C.

The reaction product is then electrophoresed on a 20% polyacrylamide/7M urea gel, then autoradiographed. The generation of shortened cleaved oligonucleotides indicates the presence of a DNA mismatch. The covalently linked enzyme is expected to show enhanced activity over unlinked enzyme, as expected from previous data (Bruice et al., 1963, Journal of American Chemical Society, vol 85:1).

EXAMPLE 7

Attachment of Glycosylase to 5' End of First Probe and AP Cleaving Enzyme to 5' End of Second Oligonucleotide A first synthetic oligonucleotide probe complementary to a region of the p53 gene is synthesized using standard phosphoramidite chemistry. Purified *E. coli* G/T mismatch enzyme is linked to the 5' end of the oligonucleotide with a linker using methods already described (Corey et al., 1987, Science, vol 238:1401; Corey et al., 1989, Journal of the American Chemical Society, vol 111:8523). This forms a covalent linkage of an oligonucleotide of specific sequence, with a linker region covalently linked to *E. coli* G/T mismatch enzyme. A second oligonucleotide is synthesized, where the sequence is near to the first oligonucleotide. This second oligonucleotide is synthesized as above with a linker which is attached to AP endonuclease (see FIG. 6a). The first oligonucleotide is radiolabeled at the 3' end using poly (A) polymerase and $^{32}$P-cordycepin. As a comparison, oligonucleotides without enzymes are prepared and treated alongside with the enzyme linked oligonucleotides.

Using chromosomal DNA prepared from ML-1 myeloid leukemia cells, dilutions of the target DNA from $10^{-1}$ to $10^{-8}$ pmol are setup. To these tubes 10 pmols of radiolabeled probe, 100 ng of purified *E. coli* G/T mismatch enzyme and 100 ng of AP endonuclease for the unlinked oligonucleotide and buffer are added. The reaction are allowed to proceed for 30 minutes at 37° C.

The reaction product is then electrophoresed on a 20% polyacrylamide/7M urea gel, then autoradiographed. The generation of shortened cleaved oligonucleotides indicates the presence of a DNA mismatch. The covalently linked enzyme is expected to show enhanced activity over unlinked enzyme, as expected from previous data (Bruice et al., 1963, Journal of American Chemical Society, vol 85:1).

EXAMPLE 8

Attachment of Glycosylase to 3' End of First Probe and AP Endonuclease to the 5' End of Second Probe and a Third Oligonucleotide is the Specific Probe A synthetic oligonucleotide (first) complementary to a region of the p53 gene is synthesized using standard phosphoramidite chemistry. Purified *E. coli* G/T mismatch enzyme is linked to the 3' end of the first oligonucleotide with a linker using methods already described (Corey et al., 1987 Science, vol 238:1401; Corey et al., 1989, Journal of the American Chemical Society, vol 111:8523). This forms a covalent linkage of an oligonucleotide of specific sequence, with a linker region covalently linked to *E. coli* G/T mismatch enzyme. A second oligonucleotide is synthesized, where the sequence is near to the first oligonucleotide but allows a space at the 3' end where a mutation probe can hybridize. This second oligonucleotide is synthesized as above with a linker which is attached to AP endonuclease. A third mutation probe is synthesized and radiolabeled at the 5' end using polynucleotide kinase and $^{32}$P-γ-ATP (see FIG. 7). As a comparison, oligonucleotides without enzymes attached are prepared and treated alongside with the enzyme linked oligonucleotides.

Using chromosomal DNA prepared from ML-1 myeloid leukemia cells, dilutions of the target DNA from $10^{-1}$ to $10^{-8}$ pmol are setup. To these tubes 10 pmols of radiolabeled probe, 100 ng of purified *E. coli* G/T mismatch enzyme and 100 ng of AP endonuclease for the unlinked oligonucleotide and buffer are added. The reaction is allowed to proceed for 30 minutes at 37° C.

The reaction product is then electrophoresed on a 20% polyacrylamide/7M urea gel, then autoradiographed. The generation of shortened cleaved oligonucleotides indicates the presence of a DNA mismatch. The covalently linked enzyme is expected to show enhanced activity over unlinked enzyme, as expected from previous data (Bruice et al., 1963, Journal of American Chemical Society, vol 85:1).

EXAMPLE 9

Attachment of the Glycosylase to the 5' End of an Oligonucleotide and AP Endonuclease to the 3' End of the Same Oligonucleotide A synthetic oligonucleotide complementary to a region of the p53 gene is synthesized using standard phosphoramidite chemistry. Purified *E. coli* G/T mismatch enzyme is linked to the 5' end of the oligonucleotide with a linker using methods already described (Corey et al., 1987, Science, vol 238:1401; Corey et al., 1989, Journal of the American Chemical Society, vol 111:8523). This forms a covalent linkage of an oligonucleotide of specific sequence, with a linker region covalently linked to *E. coli* G/T mismatch enzyme. AP endonuclease (see FIG. 8) is attached to the same oligonucleotide at the 3' end. As a comparison, oligonucleotides without enzymes are prepared and treated alongside with the enzyme linked oligonucleotides.

Using chromosomal DNA prepared from ML-1 myeloid leukemia cells, dilutions of the target DNA from $10^{-1}$ to $10^{-8}$ pmol are setup. To these tubes 10 pmols of radiolabeled probe, 100 ng of purified *E. coli* G/T mismatch enzyme and 100 ng of AP endonuclease for the unlinked oligonucleotide and buffer are added. The reaction is allowed to proceed for 30 minutes at 37° C.

The reaction product is then electrophoresed on a 50 μm i.d.×35.5 cm Supelco H-75 methyl coated borosilicate capillary containing TreviSol™ CE B (Trevigen, Inc.). 40 μl of the reaction product is applied electrokinetically to the capillary, then electrophoresed at −140 V/cm for about 12 minutes. The synthetic oligonucleotides are detected by UV detection. The generation of shortened cleaved oligonucleotides indicates the presence of a DNA mismatch. The covalently linked enzyme is expected to show enhanced activity over unlinked enzyme, as expected from previous data (Bruice et al., 1963, Journal of American Chemical Society, vol 85:1).

EXAMPLE 10

Attachment of the Glycosylase Without Associated AP Endonuclease to the 5' End of an Oligonucleotide A synthetic oligonucleotide complementary to a region of the p53 gene is synthesized using standard phosphoramidite chemistry. Purified *E. coli* G/T mismatch enzyme is linked to the 5' end of the oligonucleotide with a linker using methods already described (Corey et al., 1987, Science, vol 238: 1401; Corey et al., 1989, Journal of the American Chemical Society, vol 111:8523). This forms a covalent linkage of an oligonucleotide of specific sequence, with a linker region covalently linked to *E. coli* G/T mismatch enzyme. The oligonucleotide is radiolabeled at the 3' end using poly (A) polymerase and $^{32}$P-cordycepin. As a comparison, oligonucleotides without enzymes are prepared and treated alongside with the enzyme linked oligonucleotides.

Using chromosomal DNA prepared from ML-1 myeloid leukemia cells, dilutions of the target DNA from $10^{-1}$ to $10^{-8}$ pmol are setup. To these tubes 10 pmols of radiolabeled probe, 100 ng of purified *E. coli* G/T mismatch enzyme for the unlinked oligonucleotide and buffer are added. The reaction is allowed to proceed for 30 minutes with the temperature being cycled from about 30° to 42° C. every two minutes to allow the probes with AP sites to fall off of the target molecule and new un-treated probes to hybridize to the target molecule. This oscillating process is known as the Mismatch Chain Reaction (MCR).

The AP cleavage is effected by treatment of the samples at high pH (adjusting the pH to a range of 8 to 14) with NaOH and higher temperatures (adjusting the temperature from a temperature range of 50° C. to 95° C.). This effects AP cleavage.

The reaction product is then electrophoresed on a 20% polyacrylamide/7M urea gel, then autoradiographed. The generation of shortened cleaved oligonucleotides indicates the presence of a DNA mismatch. The covalently linked enzyme is expected to show enhanced activity over unlinked enzyme, as expected from previous data (Bruice et al., 1963, Journal of American Chemical Society, vol 85:1).

EXAMPLE 11

Attachment of Different Glycosylases to the 5' End of Oligonucleotides, Which Have Different Flourophores Present A synthetic oligonucleotide sequence complementary to a region of the p53 gene is synthesized using standard phosphoramidite chemistry. Different specific syntheses of this sequence are made with the attachment of different fluorophores (fluorescein (488 nm), rhodamine (546 nm), coumarin (365 nm)) at the 3' end of the molecule. At different wavelengths, these different fluorescent molecules can be differentiated from each other. With a linker intermediate, three different glycosylases are specifically added to three different oligonucleotide-fluorophore molecules, respectively. The three glycosylases are mutY (A/G and A/C mispairs), Thymine mismatch (also called G/T mismatch) and All type enzyme (all mispairs). The glycosylase/linker attachment is done using methods already described (Corey et al., 1987, Science, vol 238:1401; Corey et al., 1989, Journal of the American Chemical Society, vol 111:8523).

Using chromosomal DNA prepared from HL-60 myeloid leukemia cells, dilutions of the target DNA from $10^{-1}$ to $10^{-8}$ pmol are setup. To these tubes 10 pmols of radiolabeled probe, 100 ng of AP endonuclease are added. The reaction was allowed to proceed for 30 minutes at 37° C.

The reaction products are then electrophoresed on a 50 μm i.d.×35.5 cm H-75 methyl coated borosilicate capillary containing TreviSol™ CE B (Trevigen, Inc.) capillary matrix. 40 μl of the reaction product is applied electrokinetically to the capillary, then electrophoresed at −140 V/cm for about 12 minutes. The synthetic oligonucleotides are detected by a UV/VIS detector. The generation of shortened cleaved oligonucleotides indicates the presence of DNA mismatch. The exact form of the mismatch is identified from the specific fluorophore indicating the respective glycosylase used in the reaction.

For a mixture of both mutant and wild type, which could occur in a biopsy sample containing both tumor sample and normal tissue sample, both forms of DNA could be present. This technique would allow differentiating between the relative amount of each form of DNA present by measuring the amounts of both forms of the oligonucleotides.

EXAMPLE 12

Attachment of Different Glycosylases to the 5' End of Oligonucleotides, Which Have Different Lengths A synthetic oligonucleotide sequence complementary to a region of the p53 gene is synthesized using standard phosphoramidite chemistry. In this example it is known that the mismatch (or no mismatch) occurs at only one position in this sequence. Different specific syntheses of this sequence are made which have slightly longer lengths at the 3' end of the molecule and where the specific base with the mismatch is synthesized as a different base at that position (e.g. one oligo is A, another oligo is C, and the final oligo is G at one base in the oligonucleotide. The oligonucleotides are 30, 32 and 34 nucleotides in length. With a linker intermediate, three different glycosylases are specifically added to the 5' end of three different oligonucleotide molecules of different lengths, respectively. The three glycosylases were mutY (A/G and A/C mispairs), Thymine mismatch (also called G/T mismatch) and All type enzyme (all mispairs). The glycosylase/linker attachment is done using methods already described (Corey et al., 1987, Science, vol 238:1401; Corey et al., 1989, Journal of the American Chemical Society, vol 111:8523). The oligonucleotides are labeled with $^{32}$P-labelled cordycepin and poly (A) polymerase at the 3' end.

Using chromosomal DNA prepared from HL-60 myeloid leukemia cells, dilutions of the target DNA from $10^{-1}$ to $10^{-8}$ pmol are setup. To these tubes 10 pmols of different radiolabeled probe are added to the target DNA, and 100 ng of AP endonuclease is added to each tube. The reaction is allowed to proceed for 30 minutes at 37° C.

The reaction products are then electrophoresed on a 20% polyacrylamide/7M urea gel. The presence of cleaved fragments in the autoradiograph indicates the presence of a mismatch. The length of the cleaved molecule, indicates which specific mismatch was present.

For a mixture of both mutant and wild type, which could occur in a biopsy sample containing both tumor sample and normal tissue sample, both forms of DNA could be present. This technique would allow differentiating between the relative amount of each form of DNA present by measuring the amounts of both forms of the oligonucleotides.

It will be apparent to those skilled in the art that various modifications and variations can be made to the processes of this invention. Thus, it is intended that the present invention covers the modifications and variations provided they fall within the scope of the appended claims and their equivalents.

All of the aforementioned documents are expressly incorporated herein by reference in their entirety.

EXAMPLE 13

Enzyme Synthesis

Bacteria and Plasmids

*Escherichia coli* JM109 is available from New England Biolabs of Beverly, Mass. and *Escherichia coli* BW415 is available form the laboratory of Dr. Richard P. Cunningham at the State University of New York. at Albany, Department of Biological Sciences. A similar strain suitable for this protocol is BW434 and it is available from the Coli Genetic Stock Center at Yale University School of Medicine, New Haven, Conn.

BW415λDE3 was made with a λDE3 lysogenization kit from Novagen Inc. of Madison, Wis. This integration allowed for the efficient expression of the T/G mismatch specific thymine-DNA glycosylase from a T7 RNA polymerase driven promoter in an endonuclease III deficient strain of *Escherichia coli*. The expression system was contained on plasmid pET14B from Novagen Inc.

Plasmid pUV2 containing the orf10 coding sequence is available from Dr. Jork Nolling, Wageningen Agricultrual University of the Netherlands, Department of Microbiology, Hesselink van Suchtelenweg 4, 6703 CT Wageningen, The Netherlands. The pUV2 plasmid contains a portion of pFV1, including the orf10 coding sequence, cloned into pUC19.

The methods for deriving plasmid pFV1 are disclosed in Nolling et al., *Nuc. Acids Res.* 20(24): 6501 (1992). Plasmid pUC19 is available from Sigma Chemical Co., of St. Louis, Mo.

Preparation and Manipulation of DNA

Plasmid DNA was prepared from JM109 by a modified alkaline lysis method. The orf10 coding sequence from pUV2 was cloned into pUC19 via a DraI-EcoRI to HincII-EcoRI ligation using restriction endonucleases and ligase (from New England Bio Labs) according to suppliers' recommendations. The gene was PCR mutagenized using Taq Polymerase from Perkin Elmer Corp. to simultaneously change a TTG start codon to ATG, create a NcoI restriction site (5' GTG GGG CTG GAT TTC CAT GGA TGA TGC TAC TAA T3' (SEQ ID NO:9) and also a BamHI site (5' GA CGG CCA GTG GAT CCA AGG GGG CTG ATG 3' (SEQ ID NO:10) outside the gene. These new restriction sites were used to clone orf10 into pET14B.

Enzyme Induction and Purification

This plasmid was transformed into *Escherichia coli* strain BW415λDE3 and selected from on ampicillin plates. Twenty four liters of cells were grown in Tryptone yeast (TY) broth supplemented with ampicilin at 37° C. to an $OD_{595}=0.5$, and induced with 1 mM IPTG for five hours. The cells were harvested by centrifugation at 17,000×g for 20 minutes to yield 100.82 grams of cell paste which was stored at −80° C. The cell pellet was thawed, and suspended in 504 ml of 50 mM Tris-HCI pH 8.0, 200 mM NaCl, 2.5 mM EDTA 0.1 mM PMSF. The cell suspension was sonicated 5×3 minutes with a Branson sonifer, and then stirred on ice for one hour. The sonicate was centrifuged at 48,000×g for 20 minutes and the supernatant was retained. Five percent polyethelenimine was added to a final concentration of 0.1% and the suspension was stirred for 1 hour and centrifuged at 48,000×g to give a supernatant with a volume of 500 mls. The supernatant was dialyzed against 4 L of 50 mM $KPO_4$ pH 7.2 overnight.

The crude extract was loaded onto an 80 ml SP Sepharose Fast Flow (Pharmacia Biotech Inc. of Piscataway, N.J.) column, washed with 100 ml of 50mM $KPO_4$ pH 7.2 and eluted with a 1 L gradient from 0 to 1M NaCl at a flow rate of 10 ml/min. The protein eluted at 0.6M NaCl as detected by 31 kD band visualized by SDS-PAGE, and a characteristic yellow color in the fractions indicative of an Fe-S cluster of the protein. The fractions containing the protein were pooled and dialyzed against 50 mM $KPO_4$ pH 6.6, loaded onto a 5 ml DNA agarose (Pharmacia Biotech Inc.) column, washed with 10 ml of 50 mM $KPO_4$ and eluted with a 100 ml gradient of 0–1M NaCl at a rate of 1 ml/min. The protein eluted at 0.8M NaCl as determined by the criteria above. Fractions containing the protein were pooled and dialyzed overnight against 50 mM $KPO_4$pH 6.6. The protein was loaded onto a 5ml SP high trap column (Pharmacia Biotech Inc.) and eluted with 1M NaCl to concentrate the protein. The extract was further concentrated to 1.5 mls with Centriprep 10 concentrators (Amicon Division, W. R. Grace & Co., of Danvers, Mass.). At this point the protein was a single band on an overloaded Coomassie stained gel and gave an $A_{410}/A_{280}$ ratio of 0.295. This protein was active in our T-G mismatch assay. The pure protein was stored in 50% glycerol at −20° C.

EXAMPLE 14

Enzyme Activity Assays

Substrates

Two oligonucleotides were synthesized:

A 5'-GCAGCGCAGTCAGCCGACG-3' (SEQ ID NO:11) and

B 5'-CGTCGGCTGGCTGCGCTGC-3' (SEQ ID NO:12))

Oligonucleotide A was labeled with $^{32}P$ ATP from New England Nuclear of Boston, Mass. using T4 Polynucleotide kinase from New England Bio Labs. The two oligonucleotides were annealed at a three to one excess of B to A on ice for one hour to generate a duplex oligonucleotide with a unique T/G mismatch.

Assays

Glycosylase activity was monitored by measuring DNA strand breakage. $^{32}P$ labeled substrate was incubated with T/G mismatch specific thymine-DNA glycosylase protein in 50 mM HEPES-KOH pH 7.5, 100 mM KCl and 1 mM EDTA at 65° C. for 45 minutes. The enzyme was inactivated with 5M urea at 100° C. for 5 minutes and then the reaction mixture was incubated in 0.15M NaOH for 15 minutes at 55° C. to create strand breaks at the site of AP sites. Loading buffer was added to the mixture and then run on a 20% acrylamide gel containing 8M urea for 2 hours at 200 volts. The gels were dried and analyzed on X-ray film. The enzyme showed a glycosylase activity against both thymine and uracil mismatched with guanine. The activity on each substrate was at roughly the same level of magnitude, with a mared decrease in activity against thymines mismatched with cytosine. Temperature assays were run in the same manner using a labeled T-G mismatch, but incubation temperatures were 25,35,45,55,65, and 75° C. Peak activity was identified at 65° C. (92.4% cleavage), with 85.9% cleavage seen at 75° C., 90.6% cleavage seen at 55° C., 84.5% cleavage seen at 45° C., 70.2% cleavage seen at 35° C. and 36% cleavage seen at 25° C. We also noted that the enzyme was active after being boiled in the absence of 5M urea.

EXAMPLE 15

Mismatch Detection Using a Thermostable Enzyme

The following synthetic oligonucleotides were synthesized using standard phosphoramidite chemistry, well known to those in the art.

5'- CGC GCC ATG GCC ATC TAC AAG CAG TCA CAG C - 3' (SEQ ID NO:13) RO561

5'- CGC GCC ATG GCC ATC TGC AAG CAG TCA CAG C - 3' (SEQ ID NO:14) RO562

3'(SEQ ID NO:15)- GCG CGG TAC CGG TAG ATG TTC GTC AGT GTC G - 5' RO563

Oligonucleotide RO563 (SEQ ID NO:15) is complementary to both RO561 (SEQ ID NO:13) and RO562 (SEQ ID NO:14), however the underlined base G in RO562 (SEQ ID NO:14) does not complement the T in RO563 (SEQ ID NO:15), forming a mismatch. The length and composition of these synthetic oligonucleotides were chosen to have a hybridization temperature around 70° C. The sequences were based on the human p53 gene, which has a mutation at the underlined G position found in the RO562 (SEQ ID NO:14) sequence.

To confirm the size and quality of all of the above synthetic oligonucleotides 10 pmols of each were radiolabeled with $^{32}$P-γ-ATP and bacteriophage polynucleotide kinase enzyme using standard methods. A portion of each of these oligonucleotides was electrophoresed on a gel. Approximately, 1 pmol of RO561, RO562, RO563 (SEQ ID NOS: 13–15, respectively) and another unrelated oligonucleotide, RO564 were electrophoresed on a 20% acrylamide/7M Urea/ 1×TBE gel, in lanes 1, 2, 3 and 4. The position of these oligonucleotides on the gel confirmed their size and quality.

Next, a set of reactions were setup in the gel with 0.5 pmol radiolabeled oligonucleotide RO563 (SEQ ID NO:15) and unlabelled oligonucleotides as follows:

lane 5 no target,
lane 6 0.5 pmol RO561,
lane 7 1 pmol RO562,
lane 8 0.1 pmol RO562,
lane 9 0.01 pmol RO562,
lane 10 0.001 pmol RO562,
lane 11 0.0001 pmol RO562,
lane 12 0.00001 pmol RO562,
lane 13 0.000001 pmol RO562,
lane 14 0.0000001 pmol RO562,
lane 15 0.00000001 pmol RO562,
lane 16 0.000000001 pmol RO562,
lane 17 0.0000000001 pmol RO562,
lane 18 0.00000000001 pmol RO562

Each reaction was setup in 50 mM HEPES, pH 7, 50 mM KCl and 1 mM EDTA, pH 8 with 3.125 ng of thermostable mismatch glycosylase made according to Example 14 in a volume of 10 μl. The reaction was allowed to proceed for about 3 hours at 60° C. The reaction was loaded onto a 20% acrylamide/7M Urea/1×TBE gel and electrophoresed at about 300 V for about 3 hours. The gel was then electrophoresed for different lengths of time.

An autoradiograph of the gel electrophoresis showed no cleavage fragment in lane 5 as was expected because there was no target oligonucleotide in that lane. Lane 6 showed no cleavage fragment because this lane contained no mismatch. Lanes 7 to 18 showed demonstrated cleavage fragments and the level of cleavage fragments decreased in proportion to the decrease in target oligonucleotide.

This experiment revealed that the use of a thermostable enzyme at elevated temperatures resulted in a level of cleavage significantly higher than that found with a mesophilic enzyme. This increased level of cleavage results in a more sensitive assay than one carried out at lower temperatures. For instance, the autoradiograph of the above experiment after a brief 3 hour exposure showed faint cleavage at 0.000001. Longer autoradiographic exposure showed further sensitivity.

Moreover, the present Example can be varied in the following ways. Probe may be present in the assay in concentrations from 1 fmol to 100 pmol. Furthermore, the probe need not be radioactively labelled, and may be labelled by other means as are known to those of skill in the art. Furthermore, the concentration of the thermostable enzyme may be present from approximately 1 to 100 ng, and finally, the buffer composition can have higher concentrations of KCl from 50 mM to 100 mM.

What is claimed is:

1. A method of detecting a point mutation in a target polynucleotide, comprising:
   (a) hybridizing at least two single-stranded oligonucleotide probes, under stringent conditions, to at least two target polynucleotides to form at least two hybrid double-stranded polynucleotides such that a mismatch occurs at the site of said point mutation, wherein said probes are complementary to a non-mutated sequence of said target polynucleotides, and attached to each probe is a different glycosylase, only one of which will effect cleavage;
   (b) producing probe fragments by cleaving one of said probe strands at said point of mismatch, wherein said cleavage is effected by one of said glycosylases and an AP cleaving enzyme; and
   (c) detecting said probe fragments.

2. A method according to claim 1, wherein a different flourophore is attached to each of said probes.

3. A method according to claim 1, wherein each of said probes is of a different length.

4. A method according to claim 1, wherein in step (a) an oligonucleotide probe with an attached AP cleaving enzyme hybridizes to said target polynucleotides at a location adjacent to said glycosylase-attached probes.

5. A method of detecting a point mutation in a target polynucleotide, comprising:
   (a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;
   (b) cleaving said probe strand of said hybrid polynucleotide at said point of mismatch with a thermostable glycosylase, to produce oligonucleotide fragments, wherein said oligonucleotide probe is designed such that said cleavage results in dissociation of said oligonucleotide fragments from said target polynucleotide spontaneously at a predetermined temperature;
   (c) repeating steps (a) and (b);
   (d) detecting said oligonucleotide fragments; and thereby
   (e) detecting said point mutation.

6. A method according to claim 5, wherein said thermostable glycosylase of step (b) is encoded by a polynucleotide comprising the DNA sequence of FIG. 11.

7. A method of detecting a sequence in a target polynucleotide, comprising the steps of:
   (a) hybridizing a single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence;
   (b) cleaving said probe strand of said hybrid polynucleotide at said point of mismatch with a thermostable glycosylase, to produce oligonucleotide fragments, wherein said oligonucleotide probe is designed such that said cleavage results in dissociation of said oligonucleotide fragments from said target polynucleotide spontaneously at a predetermined temperature;
   (c) repeating steps (a) and (b);
   (d) detecting said oligonucleotide fragments produced by said cleavage; and thereby
   (e) detecting said sequence in said target polynucleotide.

8. A method according to claim 7, wherein said thermostable glycosylase of step (b) is encoded by a polynucleotide comprising the DNA sequence of FIG. 11.

9. A method of detecting a point mutation in a target polynucleotide, comprising:
   (a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;
   (b) cleaving said probe strand of said hybrid polynucleotide at said point of mismatch with a nucleic acid repair enzyme, to produce oligonucleotide fragments, wherein said oligonucleotide probe is designed such that said cleavage results in dissociation of said oligonucleotide fragments from said target polynucleotide spontaneously at a predetermined temperature;
   (c) repeating steps (a) and (b);
   (d) detecting said oligonucleotide fragments; and thereby
   (e) detecting said point mutation.

10. A method according to claim 9, wherein said cleaving of step (b) is effected by a enzyme from the group consisting of mutY, T/G mismatch-specific nicking enzyme, human or yeast all-type enzyme, and deoxyinosine 3'-endonuclease from E. coli.

11. A method according to claim 10, wherein said enzyme is combined with DNA lyase or DNA AP endonuclease.

12. A method of detecting a point mutation in a target polynucleotide, comprising:
   (a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;
   (b) cleaving said probe strand of said hybrid polynucleotide at said point of mismatch with a glycosylase attached to said probe employed in combination with an AP cleaving enzyme, to produce oligonucleotide fragments, wherein said oligonucleotide probe is designed such that said cleavage results in dissociation of said oligonucleotide fragments from said target polynucleotide spontaneously at a predetermined temperature;
   (c) repeating steps (a) and (b);
   (d) detecting said oligonucleotide fragments; and thereby
   (e) detecting said point mutation.

13. A method according to claim 12, wherein said AP cleaving enzyme of step (b) is attached to said probe.

14. A method according to claim 12, wherein in step (a) a second oligonucleotide probe is hybridized to said target polynucleotide at a location adjacent to said first probe, and wherein said cleaving of step (b) is effected by said glycosylase attached to said first probe and said AP cleaving enzyme attached to said second probe.

15. A method of detecting a sequence in a target polynucleotide, comprising the steps of:
   (a) hybridizing a single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence;
   (b) cleaving said probe strand of said hybrid polynucleotide at said point of mismatch with a nucleic acid repair enzyme attached to said probe, to produce oligonucleotide fragments, wherein said oligonucleotide probe is designed such that said cleavage results in dissociation of said oligonucleotide fragments from said target polynucleotide spontaneously at a predetermined temperature;

(c) repeating steps (a) and (b);

(d) detecting said oligonucleotide fragments produced by said cleavage; and thereby (e) detecting said sequence in said target polynucleotide.

16. A method according to claim 15, wherein said cleaving of step (b) is effected by a enzyme from the group consisting of mutY, T/G mismatch-specific nicking enzyme, human or yeast all-type enzyme, and deoxyinosine 3'-endonuclease from *E. coli*.

17. A method according to claim 16, wherein said enzyme is combined with DNA lyase or DNA AP endonuclease.

18. A method of detecting a sequence in a target polynucleotide, comprising the steps of:

(a) hybridizing a single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence;

(b) cleaving said probe strand of said hybrid polynucleotide at said point of mismatch with a glycosylase attached to said probe employed in combination with an AP cleaving enzyme, to produce oligonucleotide fragments, wherein said oligonucleotide probe is designed such that said cleavage results in dissociation of said oligonucleotide fragments from said target polynucleotide spontaneously at a predetermined temperature;

(c) repeating steps (a) and (b);

(d) detecting said oligonucleotide fragments produced by said cleavage; and thereby (e) detecting said sequence in said target polynucleotide.

19. A method according to claim 18, wherein said AP cleaving enzyme is attached to said probe.

20. A method according to claim 18, wherein in step (a) a second oligonucleotide probe is hybridized to said target polynucleotide at a location adjacent to said first probe, and wherein said cleaving of step (b) is effected by said glycosylase attached to said first probe and said AP cleaving enzyme attached to said second probe.

21. A method of detecting a point mutation in a target polynucleotide, comprising:

(a) hybridizing a first single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;

(b) hybridizing a second and third single-stranded oligonucleotide probe to said target polynucleotide at a location adjacent to said first probe, and wherein a glycosylase is attached to said second single-stranded probe and an AP cleaving enzyme is attached to said third single-stranded probe;

(c) cleaving said probe strand of said hybrid polynucleotide at said point of mismatch with said glycosylase and AP cleaving enzymes, to produce oligonucleotide fragments, wherein said oligonucleotide probe is designed such that said cleavage results in dissociation of said oligonucleotide fragments from said target polynucleotide spontaneously at a predetermined temperature;

(d) repeating steps (a), (b) and (c);

(e) detecting said oligonucleotide fragments; and thereby (f) detecting said point mutation.

22. A method of detecting a sequence in a target polynucleotide, comprising the steps of:

(a) hybridizing a single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence;

(b) hybridizing a second and third single-stranded oligonucleotide probe to said target polynucleotide at a location adjacent to said first probe, and wherein a glycosylase is attached to said second single-stranded probe and an AP cleaving enzyme is attached to said third single-stranded probe;

(c) cleaving said probe strand of said hybrid polynucleotide at said point of mismatch with said glycosylase and AP cleaving enzymes, to produce oligonucleotide fragments, wherein said oligonucleotide probe is designed such that said cleavage results in dissociation of said oligonucleotide fragments from said target polynucleotide spontaneously at a predetermined temperature;

(d) repeating steps (a), (b) and (c);

(e) detecting said oligonucleotide fragments produced by said cleavage; and thereby (f) detecting said sequence in said target polynucleotide.

23. A method of detecting a point mutation in a target polynucleotide, comprising:

(a) hybridizing a single-stranded oligonucleotide probe, under stringent conditions, to said target polynucleotide to form a hybrid double-stranded polynucleotide such that a mismatch occurs at the site of said point mutation, wherein said probe is complementary to a non-mutated sequence of said target polynucleotide;

(b) cleaving said probe strand of said hybrid polynucleotide at said point of mismatch with a glycosylase attached to said probe employed in combination with basic conditions and increased temperature, to produce oligonucleotide fragments, wherein said oligonucleotide probe is designed such that said cleavage results in dissociation of said oligonucleotide fragments from said target polynucleotide spontaneously at a predetermined temperature;

(c) repeating steps (a) and (b);

(d) detecting said oligonucleotide fragments; and thereby (e) detecting said point mutation.

24. A method of detecting a sequence in a target polynucleotide, comprising the steps of:

(a) hybridizing a single-stranded oligonucleotide probe, under stringent conditions, to said target polynucleotide to form a hybrid double-stranded polynucleotide, wherein said probe contains a mismatched or repairable base sequence, such that a mismatch occurs at the site of said mismatched or repairable base sequence;

(b) cleaving said probe strand of said hybrid polynucleotide at said point of mismatch with a glycosylase attached to said probe employed in combination with basic conditions and increased temperature, to produce oligonucleotide fragments, wherein said oligonucleotide probe is designed such that said cleavage results in dissociation of said oligonucleotide fragments from said target polynucleotide spontaneously at a predetermined temperature;

(c) repeating steps (a) and (b);
(d) detecting said oligonucleotide fragments produced by said cleavage; and thereby
(e) detecting said sequence in said target polynucleotide.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:

( A ) LENGTH: 15 amino acids (B) TYPE: amino acid
(C) STRANDEDNESS: single
(D) TOPOLOGY: linear (xi) SEQUENCE DESCRIPTION: SEQ ID NO:1:

```
Pro Tyr Val Ile Leu Ile Thr Glu Ile Leu Leu Arg Arg Thr Thr
 1               5                  10                  15
```

(2) INFORMATION FOR SEQ ID NO:2:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:2:

```
Ala Ile Leu Asp Leu Pro Gly Val Gly Lys Tyr Thr
 1               5                  10
```

(2) INFORMATION FOR SEQ ID NO:3:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:3:

```
Met Val Asp Ala Asn Phe Val Arg Val Ile Asn Arg
 1               5                  10
```

(2) INFORMATION FOR SEQ ID NO:4:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:4:

CCGAGGAATT AGCCTTCTG                                            19

(2) INFORMATION FOR SEQ ID NO:5:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:5:

GCAGAAGGCG AATTCCTCG                                            19

(2) INFORMATION FOR SEQ ID NO:6:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:6:

CCGAGGAATT AGCCTTCTG                                            19

(2) INFORMATION FOR SEQ ID NO:7:

(i) SEQUENCE CHARACTERISTICS:

(A) LENGTH: 19 base pairs
(B) TYPE: nucleic acid
(C) STRANDEDNESS: single
(D) TOPOLOGY: linear (x i) SEQUENCE DESCRIPTION: SEQ ID NO:7:

CCGAGGAATT CGCCTTCTG 19

(2) INFORMATION FOR SEQ ID NO:8:

(i) SEQUENCE CHARACTERISTICS:
(A) LENGTH: 19 base pairs
(B) TYPE: nucleic acid
(C) STRANDEDNESS: single
(D) TOPOLOGY: linear (x i) SEQUENCE DESCRIPTION: SEQ ID NO:8:

GCAGAAGGCG AATTCCTCG 19

(2) INFORMATION FOR SEQ ID NO:9:

(i) SEQUENCE CHARACTERISTICS:
(A) LENGTH: 34 base pairs
(B) TYPE: nucleic acid
(C) STRANDEDNESS: single
(D) TOPOLOGY: linear (x i) SEQUENCE DESCRIPTION: SEQ ID NO:9:

GTGGGGCTGG ATTTCCATGG ATGATGCTAC TAAT 34

(2) INFORMATION FOR SEQ ID NO:10:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:10:

CGACGGCCAG TGGATCCAAG GGGGCTGATG 30

(2) INFORMATION FOR SEQ ID NO:11:

(i) SEQUENCE CHARACTERISTICS:
(A) LENGTH: 19 base pairs
(B) TYPE: nucleic acid
(C) STRANDEDNESS: single
(D) TOPOLOGY: linear (x i) SEQUENCE DESCRIPTION: SEQ ID NO:11:

GCAGCGCAGT CAGCCGACG 19

(2) INFORMATION FOR SEQ ID NO:12:

(i) SEQUENCE CHARACTERISTICS:
(A) LENGTH: 19 base pairs
(B) TYPE: nucleic acid
(C) STRANDEDNESS: single
(D) TOPOLOGY: linear (x i) SEQUENCE DESCRIPTION: SEQ ID NO:12:

CGTCGGCTGG CTGCGCTGC 19

(2) INFORMATION FOR SEQ ID NO:13:

(i) SEQUENCE CHARACTERISTICS:
(A) LENGTH: 31 base pairs
(B) TYPE: nucleic acid (C) STRANDEDNESS: single
(D) TOPOLOGY: linear (x i) SEQUENCE DESCRIPTION: SEQ ID NO:13:

CGCGCCATGG CCATCTACAA GCAGTCACAG C                     31

(2) INFORMATION FOR SEQ ID NO:14:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (x i) SEQUENCE DESCRIPTION: SEQ ID NO:14:

CGCGCCATGG CCATCTGCAA GCAGTCACAG C                     31

(2) INFORMATION FOR SEQ ID NO:15:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (x i) SEQUENCE DESCRIPTION: SEQ ID NO:15:

GCGCGGTACC GGTAGATGTT CGTCAGTGTC G                     31

(2) INFORMATION FOR SEQ ID NO:16:

(i) SEQUENCE CHARACTERISTICS:
    (A) LENGTH: 666 base pairs
    (B) TYPE: nucleic acid
    (C) STRANDEDNESS: single
    (D) TOPOLOGY: linear (i x) FEATURE:
    (A) NAME/KEY: CDS
    (B) LOCATION: 1..663

(x i) SEQUENCE DESCRIPTION: SEQ ID NO:16:

| ATG | GAT | GAT | GCT | ACT | AAT | AAA | AAA | AGG | AAA | GTC | TTC | GTT | AGC | ACC | ATA | 48 |
| Met | Asp | Asp | Ala | Thr | Asn | Lys | Lys | Arg | Lys | Val | Phe | Val | Ser | Thr | Ile | |
| 1 | | | | 5 | | | | | 10 | | | | | 15 | | |

| CTT | ACG | TTT | TGG | AAT | ACA | GAT | AGG | CGC | GAC | TTT | CCT | TGG | AGG | CAT | ACG | 96 |
| Leu | Thr | Phe | Trp | Asn | Thr | Asp | Arg | Arg | Asp | Phe | Pro | Trp | Arg | His | Thr | |
| | | | 20 | | | | | 25 | | | | | 30 | | | |

| AGG | GAC | CCC | TAT | GTA | ATT | TTA | ATA | ACG | GAA | ATC | CTA | CTT | CGC | AGG | ACA | 144 |
| Arg | Asp | Pro | Tyr | Val | Ile | Leu | Ile | Thr | Glu | Ile | Leu | Leu | Arg | Arg | Thr | |
| | | 35 | | | | | 40 | | | | | 45 | | | | |

| ACT | GCG | GGG | CAT | GTT | AAA | AAG | ATA | TAT | GAC | AAG | TTT | TTT | GTT | AAG | TAC | 192 |
| Thr | Ala | Gly | His | Val | Lys | Lys | Ile | Tyr | Asp | Lys | Phe | Phe | Val | Lys | Tyr | |
| | 50 | | | | | 55 | | | | | 60 | | | | | |

| AAG | TGC | TTT | GAG | GAT | ATA | TTA | AAA | ACG | CCA | AAA | TCA | GAA | ATC | GCC | AAA | 240 |
| Lys | Cys | Phe | Glu | Asp | Ile | Leu | Lys | Thr | Pro | Lys | Ser | Glu | Ile | Ala | Lys | |
| 65 | | | | | 70 | | | | | 75 | | | | | 80 | |

| GAC | ATA | AAA | GAA | ATC | GGA | CTC | TCT | AAC | CAA | AGG | GCA | GAA | CAG | CTA | AAA | 288 |
| Asp | Ile | Lys | Glu | Ile | Gly | Leu | Ser | Asn | Gln | Arg | Ala | Glu | Gln | Leu | Lys | |
| | | | | 85 | | | | | 90 | | | | | 95 | | |

| GAA | CTG | GCA | AGG | GTC | GTC | ATA | AAT | GAT | TAT | GGG | GGC | AGA | GTG | CCC | CGA | 336 |
| Glu | Leu | Ala | Arg | Val | Val | Ile | Asn | Asp | Tyr | Gly | Gly | Arg | Val | Pro | Arg | |
| | | | 100 | | | | | 105 | | | | | 110 | | | |

| AAT | AGG | AAG | GCA | ATT | TTA | GAT | CTA | CCA | GGA | GTT | GGC | AAA | TAC | ACT | TGT | 384 |
| Asn | Arg | Lys | Ala | Ile | Leu | Asp | Leu | Pro | Gly | Val | Gly | Lys | Tyr | Thr | Cys | |
| | | 115 | | | | | 120 | | | | | 125 | | | | |

```
GCT  GCA  GTT  ATG  TGT  TTG  GCA  TTT  GGC  AAA  AAA  GCC  GCT  ATG  GTC  GAT          432
Ala  Ala  Val  Met  Cys  Leu  Ala  Phe  Gly  Lys  Lys  Ala  Ala  Met  Val  Asp
     130                      135                      140

GCA  AAT  TTT  GTG  AGA  GTT  ATT  AAC  AGG  TAC  TTT  GGG  GGA  AGC  TAT  GAA          480
Ala  Asn  Phe  Val  Arg  Val  Ile  Asn  Arg  Tyr  Phe  Gly  Gly  Ser  Tyr  Glu
145                      150                      155                      160

AAC  CTG  AAC  TAC  AAC  CAC  AAG  GCC  CTG  TGG  GAA  CTT  GCG  GAG  ACC  CTT          528
Asn  Leu  Asn  Tyr  Asn  His  Lys  Ala  Leu  Trp  Glu  Leu  Ala  Glu  Thr  Leu
               165                      170                      175

GTA  CCT  GGC  GGA  AAG  TGC  AGG  GAC  TTT  AAC  CTT  GGT  TTA  ATG  GAC  TTT          576
Val  Pro  Gly  Gly  Lys  Cys  Arg  Asp  Phe  Asn  Leu  Gly  Leu  Met  Asp  Phe
               180                      185                      190

TCC  GCA  ATC  ATA  TGT  GCC  CCA  AGA  AAG  CCA  AAG  TGT  GAG  AAA  TGT  GGG          624
Ser  Ala  Ile  Ile  Cys  Ala  Pro  Arg  Lys  Pro  Lys  Cys  Glu  Lys  Cys  Gly
          195                      200                      205

ATG  AGC  AAA  CTC  TGT  AGC  TAC  TAT  GAG  AAG  TGT  AGT  ACT  TGA                    666
Met  Ser  Lys  Leu  Cys  Ser  Tyr  Tyr  Glu  Lys  Cys  Ser  Thr
     210                      215                      220
```

( 2 ) INFORMATION FOR SEQ ID NO:17:

( i ) SEQUENCE CHARACTERISTICS:
        ( A ) LENGTH: 221 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met  Asp  Asp  Ala  Thr  Asn  Lys  Lys  Arg  Lys  Val  Phe  Val  Ser  Thr  Ile
 1                  5                   10                      15

Leu  Thr  Phe  Trp  Asn  Thr  Asp  Arg  Arg  Asp  Phe  Pro  Trp  Arg  His  Thr
               20                      25                      30

Arg  Asp  Pro  Tyr  Val  Ile  Leu  Ile  Thr  Glu  Ile  Leu  Leu  Arg  Arg  Thr
               35                      40                      45

Thr  Ala  Gly  His  Val  Lys  Lys  Ile  Tyr  Asp  Lys  Phe  Phe  Val  Lys  Tyr
     50                      55                      60

Lys  Cys  Phe  Glu  Asp  Ile  Leu  Lys  Thr  Pro  Lys  Ser  Glu  Ile  Ala  Lys
65                        70                      75                       80

Asp  Ile  Lys  Glu  Ile  Gly  Leu  Ser  Asn  Gln  Arg  Ala  Glu  Gln  Leu  Lys
               85                      90                      95

Glu  Leu  Ala  Arg  Val  Val  Ile  Asn  Asp  Tyr  Gly  Gly  Arg  Val  Pro  Arg
               100                     105                     110

Asn  Arg  Lys  Ala  Ile  Leu  Asp  Leu  Pro  Gly  Val  Gly  Lys  Tyr  Thr  Cys
          115                     120                     125

Ala  Ala  Val  Met  Cys  Leu  Ala  Phe  Gly  Lys  Lys  Ala  Ala  Met  Val  Asp
     130                     135                     140

Ala  Asn  Phe  Val  Arg  Val  Ile  Asn  Arg  Tyr  Phe  Gly  Gly  Ser  Tyr  Glu
145                     150                     155                      160

Asn  Leu  Asn  Tyr  Asn  His  Lys  Ala  Leu  Trp  Glu  Leu  Ala  Glu  Thr  Leu
               165                     170                     175

Val  Pro  Gly  Gly  Lys  Cys  Arg  Asp  Phe  Asn  Leu  Gly  Leu  Met  Asp  Phe
               180                     185                     190

Ser  Ala  Ile  Ile  Cys  Ala  Pro  Arg  Lys  Pro  Lys  Cys  Glu  Lys  Cys  Gly
          195                     200                     205

Met  Ser  Lys  Leu  Cys  Ser  Tyr  Tyr  Glu  Lys  Cys  Ser  Thr
     210                     215                     220
```